United States Patent
Degtyar et al.

(10) Patent No.: US 12,239,561 B2
(45) Date of Patent: Mar. 4, 2025

(54) FOOT ORTHOSIS

(71) Applicant: TECHNION RESEARCH & DEVELOPMENT FOUNDATION LIMITED, Haifa (IL)

(72) Inventors: Andrey Degtyar, Haifa (IL); Oleg Shlomo Gendelman, Haifa (IL)

( * ) Notice: Subject to any disclaimer, the term of this patent is extended or adjusted under 35 U.S.C. 154(b) by 675 days.

(21) Appl. No.: 17/435,503

(22) PCT Filed: Mar. 5, 2020

(86) PCT No.: PCT/IL2020/050263
§ 371 (c)(1),
(2) Date: Sep. 1, 2021

(87) PCT Pub. No.: WO2020/178839
PCT Pub. Date: Sep. 10, 2020

(65) Prior Publication Data
US 2022/0133517 A1    May 5, 2022

Related U.S. Application Data

(60) Provisional application No. 62/813,894, filed on Mar. 5, 2019.

(51) Int. Cl.
*A61F 5/01*    (2006.01)
(52) U.S. Cl.
CPC ..... *A61F 5/0113* (2013.01); *A61F 2005/0197* (2013.01)
(58) Field of Classification Search
CPC ........ A61F 5/0113; A61F 5/01; A61F 5/0127; A61F 5/00; A61F 5/0111; A61F 5/019;
(Continued)

(56) References Cited

U.S. PATENT DOCUMENTS

| 6,025 | A | 1/1849 | Hibbert |
| 48,279 | A | 6/1865 | Hoover |

(Continued)

FOREIGN PATENT DOCUMENTS

EP    2922506 A2    9/2015

OTHER PUBLICATIONS

Binder-Macleod SA, Snyder-Mackler L. Muscle fatigue: clinical implications for fatigue assessment and neuromuscular electrical stimulation. Phys Ther. Dec. 1993;73(12):902-10. doi: 10.1093/ptj/73.12.902. PMID: 8248298.

(Continued)

*Primary Examiner* — Alireza Nia
*Assistant Examiner* — Daniel A Miller
(74) *Attorney, Agent, or Firm* — The Roy Gross Law Firm, LLC; Roy Gross

(57) ABSTRACT

Apparatus (20, 200) including a leaf spring assembly (22, 220) shaped to define a first end (32), a second end (34), and a middle portion (36) including a plurality of layered leaf springs (40). The spring is placed across a joint such that the first end is placed against a first location on a first side of the joint, and the second end is placed against a second location on a second side of the joint. When the leaf spring is constrained between the first and second locations, the middle portion (36) bridges a gap (120) formed between the middle portion and the joint. Additionally, a position of a first portion of a limb on the first side of the joint is maintained at a desired angle with respect to a second portion of the limb on the second side of the joint. Other embodiments are also described.

17 Claims, 14 Drawing Sheets

(58) Field of Classification Search
CPC ...... A61F 5/0104; A61F 5/0585; A61F 5/058;
A61F 5/37; A61F 5/05841; A61F 5/0102;
A61F 2005/0197; A61F 2005/0165; A61F
2005/0153; A61F 2005/0167; A61F
2005/0179; A43B 7/20; A41D 13/05;
A41D 13/0543; A41D 13/06; A61H 3/00;
A61H 3/001; A61H 3/007
USPC .......................................................... 602/28
See application file for complete search history.

(56) References Cited

U.S. PATENT DOCUMENTS

| | | | |
|---|---|---|---|
| 60,210 A | 12/1866 | Luther et al. | |
| 60,216 A | 12/1866 | Martindale | |
| 60,223 A | 12/1866 | Morrill | |
| 60,227 A | 12/1866 | Myers | |
| 60,228 A | 12/1866 | Myers | |
| 60,229 A | 12/1866 | Myers | |
| 60,265 A | 12/1866 | Sawyer | |
| 128,882 A | 7/1872 | Hunt | |
| 482,124 A | 9/1892 | Gunning | |
| D24,192 S | 4/1895 | Buckius | |
| 1,635,230 A * | 7/1927 | Spicer | A61F 5/50 602/5 |
| 7,125,392 B2 | 10/2006 | Scott | |
| 8,348,810 B2 * | 1/2013 | Land | A63B 21/4025 602/5 |
| 8,357,110 B1 * | 1/2013 | Frierson | A61F 5/0113 602/23 |
| 2007/0197948 A1 * | 8/2007 | Ingimundarson | A61F 5/14 602/27 |
| 2011/0196275 A1 | 8/2011 | Chang et al. | |
| 2015/0305911 A1 * | 10/2015 | Schroeder | A61F 5/0113 602/28 |
| 2017/0196720 A1 * | 7/2017 | Hassel | A61F 5/0113 |
| 2018/0042752 A1 | 2/2018 | Omarsson et al. | |
| 2019/0000659 A1 * | 1/2019 | Storup | B32B 7/08 |

OTHER PUBLICATIONS

Degtyar, A. (2017). Flexible and Adaptable Ankle Foot Orthosis for Walking Style Correction of Post Stroke Patients [M.Sc thesis abstract]. Technion—Israel Institute of Technology.

Degtyar, A. (2017). Flexible and Adaptable Ankle Foot Orthosis for Walking Style Correction of Post Stroke Patients [MS Thesis]. Technion—Israel Institute of Technology.

PCT International Search Report for International Application No. PCT/IL2020/050263, mailed May 12, 2020, 3pp.

PCT Written Opinion for International Application No. PCT/IL2020/050263, mailed May 12, 2020, 5pp.

PCT International Preliminary Report on Patentability for International Application No. PCT/IL2020/050263, issued Aug. 25, 2021, 6pp.

* cited by examiner

FOOT ORTHOSIS

CROSS REFERENCE TO RELATED APPLICATIONS

This application is a National Phase of PCT Patent Application No. PCT/IL2020/050263 having International filing date of Mar. 5, 2020, which claims the benefit of priority under 35 USC § 119 (e) of U.S. Provisional Patent Application No. 62/813,894 filed on Mar. 5, 2019, the contents of which are incorporated herein by reference in their entirety.

FIELD OF THE INVENTION

Some embodiments of the present invention relate generally to orthotic devices and more specifically to an ankle foot orthosis.

BACKGROUND

Foot drop is a symptom of muscular weakness typically caused by nerve injury, muscle or nerve disorders and/or brain and spinal cord disorders. Affected patients demonstrate abnormal gait patterns in which dorsiflexion and eversion of the ankle do not occur voluntarily. In other words, foot drop is characterized by inability or impaired ability to raise the foot from the ankle and/or move the foot at the ankle inward and outward to properly align the heel with the leg. Foot drop generally leads to walking instability and probable falling as a result of the forefoot drag or/and foot collision with the ground.

An orthosis is an externally applied device configured to assist in correcting impaired structure and function of the neuromuscular and skeletal system.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

Apparatus and method are provided for maintaining a body portion at a desired position with respect to another, adjacent, body portion using a spring, in accordance with some embodiments of the present invention.

Typically, apparatus is provided comprising a spring, e.g., a leaf spring, shaped and sized to be placed across a joint of a user such that a first end of the leaf spring is placed against a first location on a first side of the joint, and a second end of the leaf spring is placed against a second location on a second side of the joint, thereby, positioning the leaf spring between the first and second locations on either side of the joint.

When the leaf spring is constrained between the first and second locations, a position of a first portion of a limb on the first side of the joint is maintained at a desired angle with respect to a second portion of the limb on the second side of the joint. Additionally, when the leaf spring is constrained between the first and second locations on both sides of the joint, the middle portion of the leaf spring typically does not contact the surface of the joint and the limb, such that a gap is formed between the middle portion and the joint and the limb. Typically, since the leaf spring does not contact the joint, the leaf spring generally does not limit ankle motion in the transverse plane, does not limit ankle joint eversion in the frontal plane and does not limit dorsiflexion in the sagittal plane.

In some embodiments, the leaf spring is configured for use with a lower portion of a leg of a user to reduce foot drop and assist in correcting gait of the user. Typically, the leaf spring is placed against an outer surface of an anterior side of a leg of a subject such that the first end of the leaf spring contacts a first location, e.g., on a shin of the user, and the second end contacts a second location, e.g., on a dorsal side of the foot of the user. When the leaf spring is constrained between the shin and the dorsal side of the foot, the middle portion of the leaf spring bridges a gap formed across the ankle joint between the middle portion and the joint, and a position of a foot of the subject is maintained at any desired angle with respect to the leg, i.e., with respect to the shin. For example, when the leaf spring is constrained between the shin and the dorsal side of the foot, plantar flexion is limited to about 10-15 degrees, e.g., to about 15 degrees, thereby reducing foot drop in the user and inhibiting, foot slap, foot drag and collision of the foot with the ground. In general, in is noted that limiting of the angle of plantar flexion can be adjusted per needs of the user.

In some embodiments, the leaf spring comprises a plurality of leaves, forming a leaf spring assembly.

In some embodiments, a configuration of a leaf spring assembly is provided comprising three linear leaf springs each comprising a plurality of leaves and positioned alongside each other. For example, the central leaf spring (which comprises a plurality of leaves) assists lifting the foot by limiting plantar flexion, and the side leaf springs (each also comprising a plurality of leaves) typically assist in correcting over-rotation of the foot and impaired eversion and inversion of the foot.

There is therefore provided in accordance with some embodiments of the present invention, apparatus including: a leaf spring assembly: (a) shaped to define a first end, a second end, and a middle portion including a plurality of layered leaf springs disposed between the first and second ends; and (b) configured to be placed across a joint of a user such that the first end is placed against a first location on a first side of the joint, and the second end is placed against a second location on a second side of the joint, and when the leaf spring is constrained between the first and second locations: (i) the middle portion bridges a gap formed between the middle portion and the joint, and (ii) a position of a first portion of a limb on the first side of the joint is maintained at a desired angle with respect to a second portion of the limb on the second side of the joint.

In some embodiments, the apparatus the joint includes an ankle joint, the first location includes a location on a shin of the subject and the second location includes a location on a dorsal side of the foot of the subject, and the leaf spring is configured to be placed against a leg such that the upper portion contacts the shin and the lower portion contacts the dorsal side of the foot, and position of a foot of the subject is maintained at a desired angle with respect to the leg.

In some embodiments, the plurality of leaf springs includes a plurality of linear leaf springs.

In some embodiments, the apparatus further includes a leaf spring-coupling element configured to couple the leaf spring to the subject.

In some embodiments, the leaf spring includes a leaf spring assembly including a first leaf spring and a second leaf spring, the second leaf spring being positioned alongside the first leaf spring.

In some embodiments, the first leaf spring has a first spring constant, and the second leaf spring has a second spring constant, the first spring constant is different from the second spring constant.

In some embodiments, the apparatus further includes a third leaf spring configured to be positioned alongside the first and second leaf springs.

There is further provided in accordance with some embodiments of the present invention, apparatus including; a leaf spring assembly: (a) shaped to define a first end, a second end, and a middle portion including a plurality of layered leaf springs disposed between the first and second ends; and (b) configured to be placed against an outer surface of an anterior side of a leg of a subject such that the first end contacts a first location and the second end contacts a second location, and when the leaf spring is constrained between the first and second locations: (i) the middle portion bridges a gap formed across the ankle joint between the middle portion and the leg, and (ii) a position of a foot of the subject is maintained at a desired angle with respect to the leg.

In some embodiments, the first location includes a shin of the subject and the second location includes a dorsal side of the foot of the subject, and the leaf spring is configured to be placed against the leg such that the upper portion contacts the shin and the lower portion contacts the dorsal side of the foot.

In some embodiments, the middle portion has a length of 10-20 cm, when the leaf spring assembly is unconstrained.

In some embodiments, each leaf has a thickness of 0.1-0.5 mm.

In some embodiments, each leaf has a weight of 5-10 grams.

In some embodiments, the leaf has a width of 5-20 mm when unconstrained.

In some embodiments, further including a leaf spring-coupling element configured to couple the leaf spring to the subject.

In some embodiments, the leaf spring-coupling element includes an upper cuff coupled to the upper portion of the leaf spring and configured to surround at least a portion of a lower leg of the subject.

In some embodiments, the leaf spring-coupling element includes a lower cuff coupled to the lower portion of the leaf spring and configured to surround an ankle of the subject.

In some embodiments, the leaf spring includes a leaf spring assembly including a first leaf spring and a second leaf spring positioned alongside the first leaf spring.

In some embodiments, the first leaf spring has a first spring constant, and the second leaf spring has a second spring constant, the first spring constant is different from the second spring constant.

In some embodiments, further including a third leaf spring configured to be positioned alongside the first and second leaf springs.

There is further provided in accordance with some embodiments of the present invention, a method including: positioning a leaf spring including a plurality of layered leaves, against first and second locations on an outer surface of an anterior side of a leg of a subject; and maintaining a position of a foot of the subject at a desired angle with respect to a shin of the subject by constraining the leaf spring between the first and second locations.

In some embodiments, maintaining a position of the foot includes limiting plantar flexion to 10-15 degrees.

In some embodiments, maintaining includes maintaining the foot at a 10-15-degree angle with respect to the leg in a sagittal plane.

In some embodiments, the first location includes a shin of the subject and the second location includes a dorsal side of the foot of the subject, and positioning includes positioning the leaf spring against the shin and the dorsal side of the foot.

In some embodiments, the leaf spring includes a first end, a second end, and a middle portion disposed between the first and second ends and positioning the leaf spring includes positioning the leaf spring against the leg such that the middle portion bridges a gap formed between the middle portion and the leg.

In some embodiments, maintaining the foot by constraining the leaf spring further includes maintaining the foot by adjusting the leaf spring to a desired spring constant.

In some embodiments, maintaining the foot by constraining the leaf spring further includes maintaining the foot by preloading the spring to a desired preload value.

In some embodiments, the leaf spring includes a leaf spring assembly, the assembly including a first leaf spring and second leaf spring, and the positioning includes positioning the second leaf spring alongside the first leaf spring.

In some embodiments, the leaf spring assembly further includes a third leaf spring and positioning includes positioning the third leaf spring on alongside the first and second leaf spring.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

In accordance with some aspects of the present invention, apparatus comprising an orthotic spring is provided for maintaining a body portion at a desired position with respect to another, adjacent, body portion.

In accordance with some aspects, the spring comprises a leaf spring.

In accordance with some aspects of the present invention, the leaf spring and leaf spring assemblies described herein supports a foot of a user at least in the frontal and/or sagittal and/or transverse planes and additionally provide knee support.

In accordance with some aspects of the present invention, the orthotic leaf spring assemblies described herein are shaped and sized for use with a portion of a lower leg of a user for correcting gait and reducing foot drop, foot slap, forefoot drag and forefoot collision with the ground, by maintaining a foot of the user at a desired angle with respect to the shin of the leg. It is noted that the orthotic leaf spring assemblies described herein are configured to maintain the foot of a user at any desired angle with respect to the shin of the leg, as determined by the needs of the user.

Specifically, in accordance with some aspects, the orthotic leaf spring assemblies described herein are configured to correct an angle between the foot and the shin of the user in the sagittal plane, such that plantar flexion is limited. Additionally, while limiting planar flexion in the sagittal plane, the leaf spring does not limit dorsiflexion in the sagittal plane and also allows for free ankle rotation, for example, in the transverse and frontal planes (e.g., allows for eversion in the frontal plane, and additionally, an inversion angle may be set to any desired value per a specific user). Additionally, the orthotic leaf springs assemblies described herein are configured to correct ankle joint rotation trajectory also during gait.

In accordance with some aspects, the orthotic leaf spring assemblies described herein are configured to limit plantar flexion of the foot of the subject such that collision of the foot with the ground, foot drag and foot slap are inhibited.

In accordance with some aspects, the orthotic leaf spring assemblies described herein are configured to assist in dorsiflexion of the foot by relieving a load from the user's muscles thereby easing and facilitating natural dorsiflexion motion of the subject.

In accordance with some aspects, the orthotic leaf spring assemblies described herein are configured to assist in dorsiflexion by lifting of the foot due to the spring action.

In accordance with some aspects, the orthotic leaf spring assemblies described herein are both corrective and rehabilitative.

In accordance with some aspects, the orthotic leaf spring assemblies described herein are shaped and sized be applied directly to a foot or to a shoe.

In accordance with some aspects, the orthotic leaf spring assemblies described herein provide optimal attachment and uniform pressure distribution.

Figure 1:
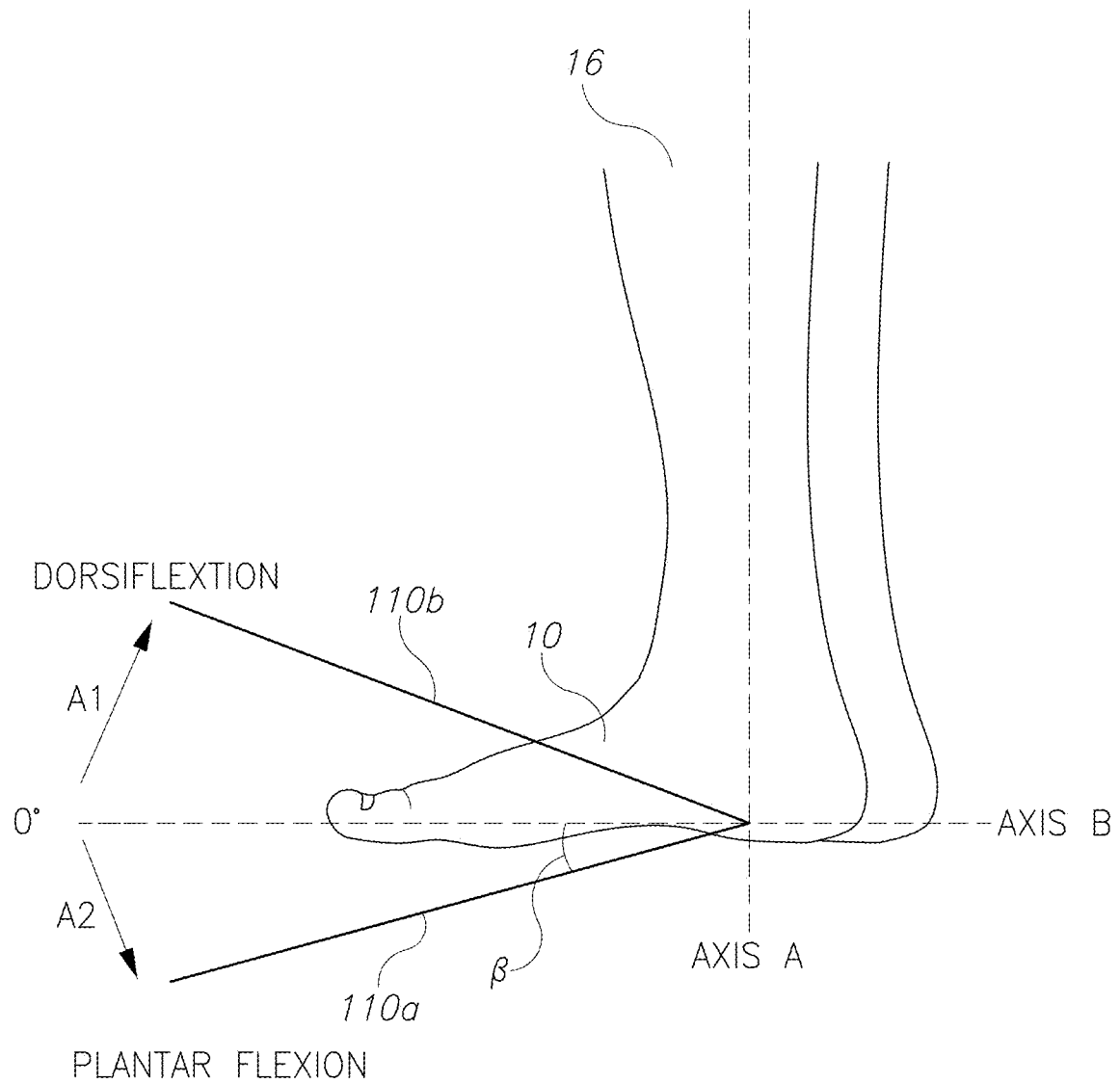
FIG. 1 is a schematic illustration depicting axes and angles referred to throughout the application.
Figure 3B:
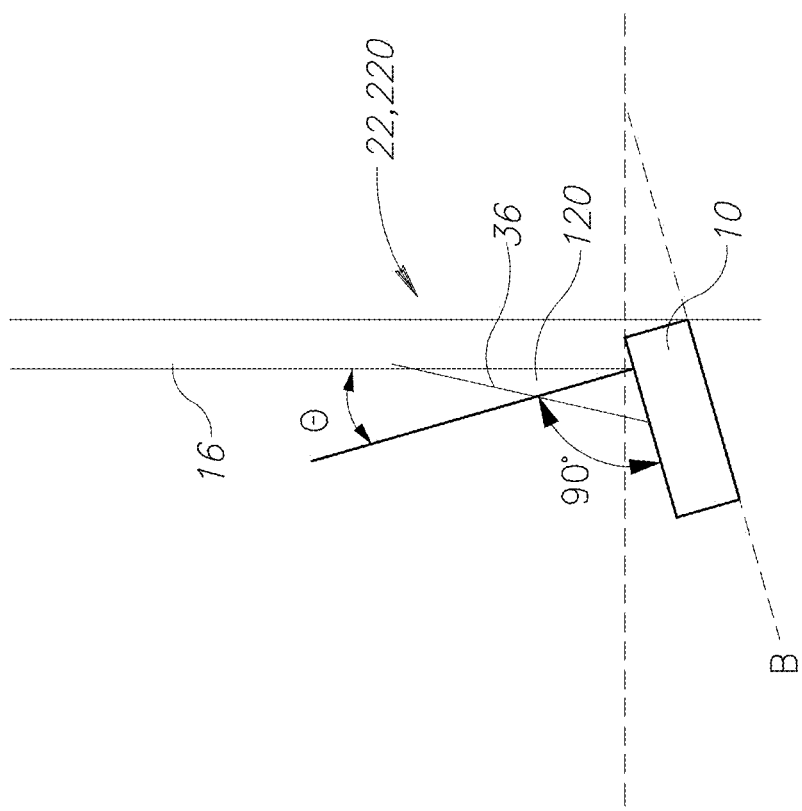
FIGS. 3A-B are schematic illustrations depicting angles referred to throughout the application, and showing the leaf spring assembly, in accordance with some embodiments of the present invention.
Figure 3A:
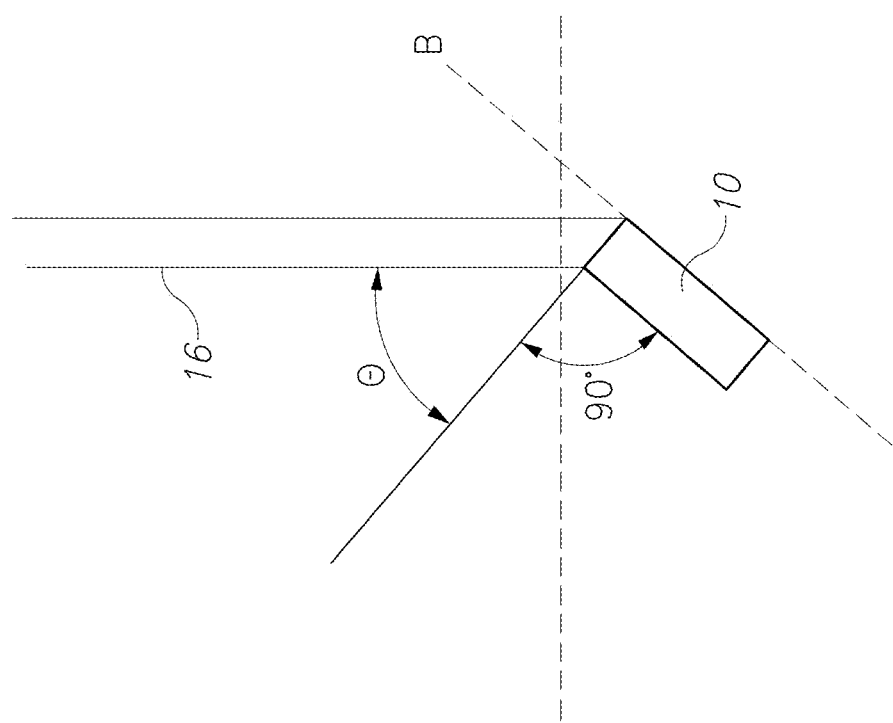

Reference is first made to FIG. 1 and FIGS. 3A-B, depicting some axes and angles referred to throughout the application. In FIG. 1 the leaf spring assemblies are omitted for clarity.

FIG. 1 indicates possible dorsiflexion motion (indicated by arrow A1, and line 110b) and plantar flexion (indicated by arrow A2 and line 110a). Plantar flexion occurs when foot 10 is positioned below Axis B (for example is aligned with line 110a and indicated by angle beta) In accordance with some embodiments of the present invention, when the leaf spring assemblies described herein are used by a user, plantar flexion of foot 10 generally does not go beyond 10-15 degrees (as shown by angle theta in FIGS. 3A-B).

Typically, subjects suffering from foot drop, exhibit impaired ability to raise the foot such that foot 10 is in a state of excessive plantar flexion, resulting in forefoot drag or/and foot slap and foot collision with the ground.

FIGS. 3A-B depict ankle angle theta which is the angle between foot 10 and shin 16 in the sagittal plane. Use of the leaf spring assemblies described hereinbelow limits angle theta to about 10-15 degrees thereby limiting plantar flexion to about 10-15 degrees and reducing foot drop.

Figure 2A:
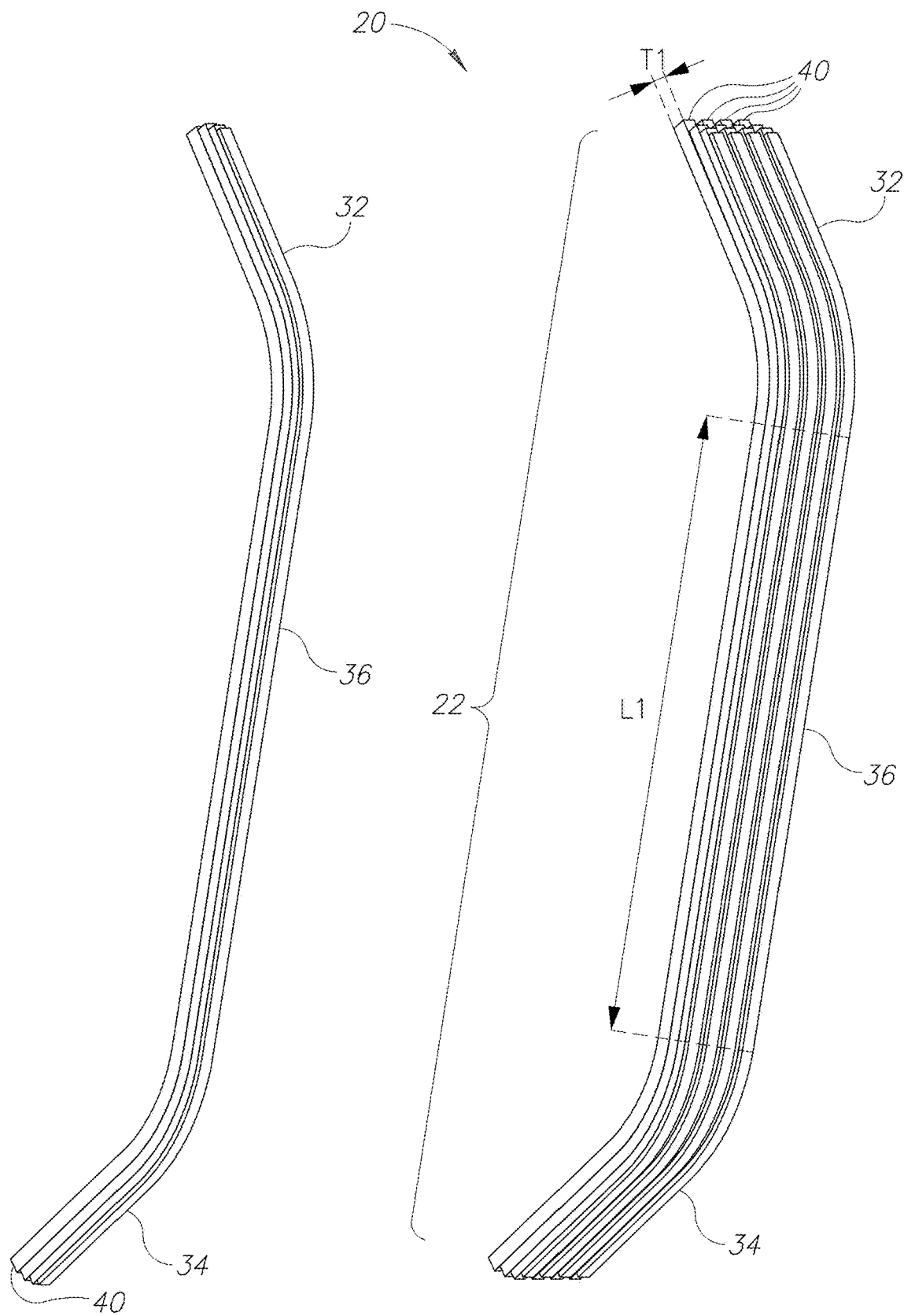
FIG. 2A is a schematic illustration of apparatus comprising a leaf spring assembly, in accordance with some embodiments of the present invention.

Reference is now made to FIG. 2A, which is a schematic illustration of apparatus 20 comprising a leaf spring assembly 22 in accordance with some embodiments of the present invention. Leaf spring assembly 22 is typically configured for maintaining a body portion at a desired position with respect to another, adjacent, body portion. For example, leaf spring assembly 22 is shaped and sized for use with a portion of a lower leg of a user for maintaining the foot at any desired angle with respect to the shin of the leg, e.g., by limiting plantar flexion, thereby reducing foot drop and facilitating correct gait.

As shown, leaf spring 22 assembly is shaped to define a first end 32, a second end 34 and a middle portion 36 disposed between first and second ends 32 and 34. In some embodiments, middle portion 36 is linear, as illustrated. For some embodiments, leaf spring assembly 22 comprises a plurality of layered elastic leaves 40, e.g., 2-20 leaves 40, e.g. 2-10 leaves 40. Typically, the plurality of layered leaves 40 are stacked against each other to form leaf spring assembly 22. In some embodiments, only one leaf 40 is used. It is noted however, that a maximum number of leaves 40 is not limited and leaf spring assembly 22 may comprise any number of leaves 40.

In some embodiments, only middle portion 36 of leaf spring assembly 22 comprises a plurality of leaves 40 (application not shown). For such embodiments, first and second ends of leaf spring assembly 22, which typically come in contact with the user, may comprise a single leaf spring or any other suitable contact surface configured to be placed against a body portion of the subject in order to anchor leaf spring assembly 22 in place against the body portion. In other embodiments, as shown in FIG. 2A, the plurality of leaves 40 extend along the entirety of leaf spring assembly 22. It is noted, however, that any portion of leaf spring assembly 22 may comprise a single leaf or any number of multiple leaves.

Typically, a length of first end 32, second end 34, and middle portion 36 may vary with respect to each other. Additionally, or alternatively, a length of first end 32, second end 34, and middle portion 36 may vary among users and/or are adjusted according to the user (e.g., adjusted according to a weight and/or height of the user) and to the location on which leaf spring assembly 22 is placed on the user's body. For some embodiments, middle portion 36 is typically greater in length than first end 32 and second end 34. For example, middle portion 36 may have a length L1 of 5-30 cm, e.g., 10-20 cm, when leaf spring 22 is unconstrained.

For some embodiments, each leaf 40 has a thickness T1 of 0.1-0.5 mm, e.g., 0.3 mm when unconstrained, and a weight of 5-10 grams, e.g., 8-9 grams, e.g., 8.7 grams. For some embodiments, leaf spring assembly 22 has a width of 1-40, mm e.g., 5-20 mm, e.g., 10-15 mm, when unconstrained. It is noted that each leaf 40 may have any suitable thickness, weight length or width.

Leaf spring 22 assembly typically has adjustable stiffness for configuring the use of leaf spring assembly 22 to each user according to individual anatomical and physiological requirements of the user.

Figure 2C:
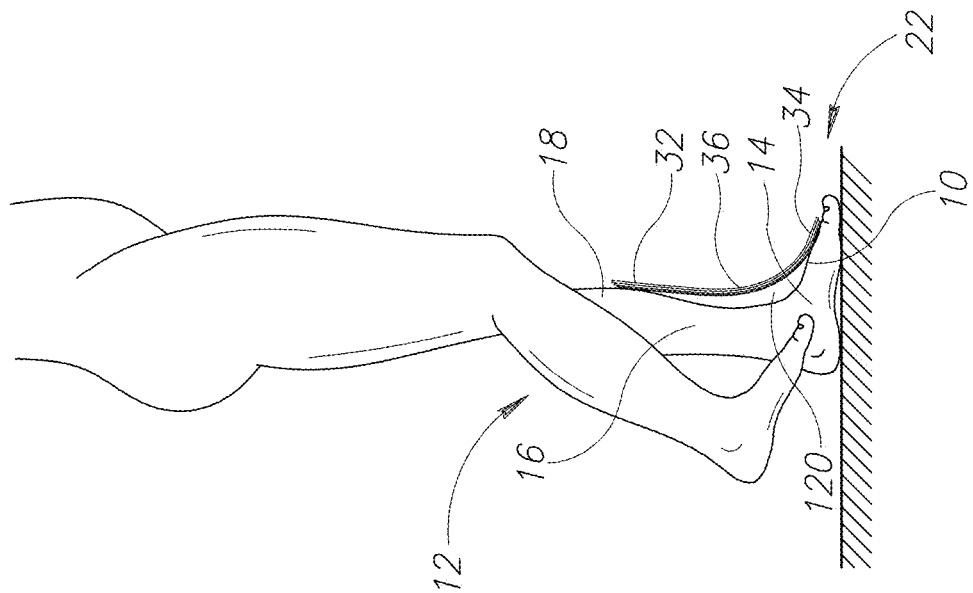
FIGS. 2B-C are schematic illustrations of the leaf spring assembly positioned on a lower leg of the subject for reducing foot drop in the subject, in accordance with some embodiments of the present invention.
Figure 2B:
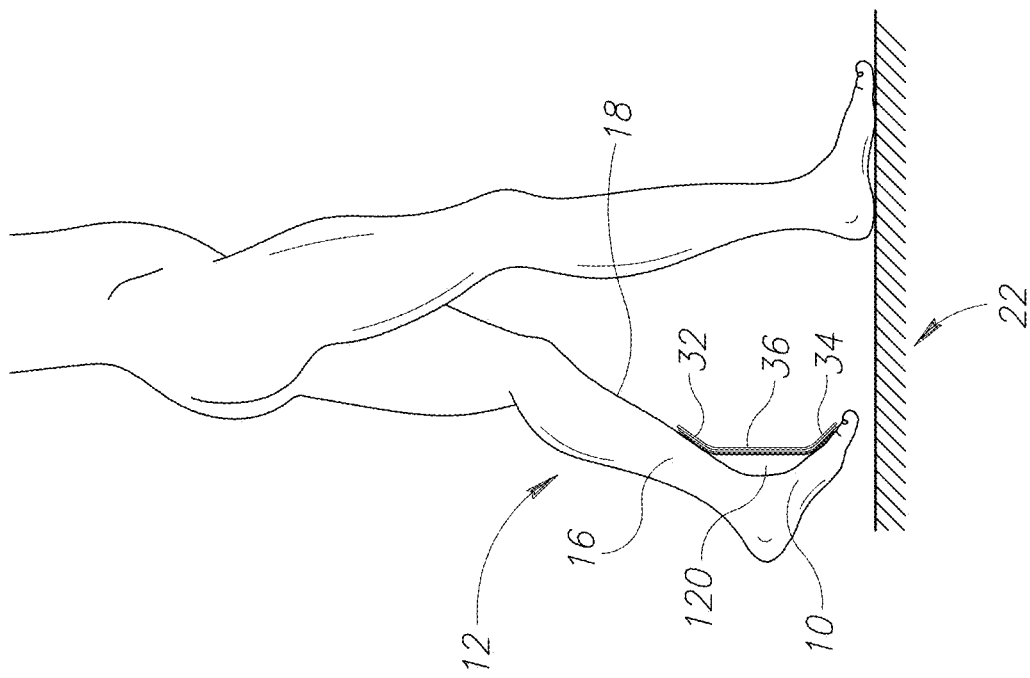

Reference is now made to FIGS. 2B-C, which are schematic illustration of side views of leaf spring assembly 22 positioned on a lower leg 12 for maintaining foot 10 at a desired angle with respect to shin 16, in accordance with some embodiments of the present invention.

Generally, leaf spring assembly 22 extends across a joint of a user and placed in contact with locations on either side of the joint but typically forms a gap between the leaf spring assembly and the joint, such that the middle portion of the leaf spring generally does not contact the joint.

As shown in FIGS. 2B-C, in some embodiments, leaf spring assembly 22 is placed against an outer surface 18 of an anterior side of shin 16 such that first end 32 is placed against a first location and second end 34 is placed against a second location. As shown, typically, the first location is a location on shin 16 and the second location is a location on a dorsal side of foot 10.

As shown, when leaf spring 22 is positioned across an ankle joint 14 of the user and leaf spring assembly 22 is constrained between the first and second locations, a gap 120 is formed between middle portion 36 and leg 12, such that middle portion 36 generally does not come in contact with ankle joint 14 and leg 12.

FIG. 2B shows leaf spring assembly 22 in an extended state. Generally, leaf spring assembly 22 facilitates limiting of plantar flexion of beyond 10-15 degrees, and generally maintains foot 10 at a desired angle with respect to the shin (i.e., ankle angle theta is about 10-15 degrees).

FIG. 2C, shows leaf spring assembly 22 in a deflected, flexed, state thereof, with plantar flexion of foot 10 being close to zero. The deflected, flexed, state of spring assembly 22 shown in FIG. 2C is typically achieved when a user continues to work the spring and lift the foot from a position in which leaf spring assembly 22 is extended and plantar flexion is at about 10-15 degrees (as shown with reference to FIG. 2B).

Further as shown in FIG. 2C. Leaf spring assembly 22 generally does not contact ankle joint 14 (even in the deflected state thereof), thus ankle joint 14 is not fixed or restricted by leaf spring assembly 22 in the transverse plane and dorsiflexion is not limited in the sagittal plane, and eversion is not limited in the frontal plane. Accordingly, use of leaf spring assembly 22 allows increased rotation amplitude of ankle joint 14 in at least in the sagittal transverse and frontal planes.

Reference is again made to FIGS. 3A-B which are schematic illustrations of the spring effect of leaf spring assembly 22 and leaf spring assembly 220 (described herein below with reference to FIGS. 4A-C), in accordance with some embodiments of the present invention.

In FIGS. 3A-B, foot 10 is represented by box 10 and shin 16 is represented by lines 16. FIG. 3A is representative of a user suffering from foot drop, showing foot 10 dropping downwards. This is in contrast to a healthy subject who is capable of (i) raising foot 10 to be perpendicular to the shin, and (ii) obtain dorsiflexion motion by further raising the foot upwards. In FIG. 3B, leaf spring 22 is in place in an extended configuration thereof (as opposed to the deflected (i.e., flexed) state shown in FIG. 2B). For clarity purposes, only middle portion 36 of leaf spring assemblies 22 and 220 is represented in FIG. 3B.

Due to placement of the leaf spring, plantar flexion of foot 10 is reduced to a desired angle theta (e.g., about 10-15 degrees) compared to the position of foot 10 without use of leaf spring 22 as shown in FIG. 3A. As shown, angle theta is corrected, i.e., limited, with use of leaf spring 22 thereby inhibiting foot drag, foot slap and collision of the foot with the ground. It is noted that when the leaf spring assembly is placed on the lower leg as shown in FIG. 3B, dropping of the foot beyond about 10-15 degrees is inhibited by geometric locking of the foot by the spring. However, it is noted that, upward motion of foot 10 is not limited by the leaf spring assemblies such that the user may continue to lift foot 10, as well as allowing full range of dorsiflexion (depending on the ability of the user.)

It is noted that allowing a range of motion by limiting plantar flexion but not fully preventing it, typically encourages a user to attempt to continue to lift foot 10 thereby contributing to rehabilitation of the user. Additionally, or alternatively, improved muscle tone of the muscles of the lower leg is maintained thereby inhibiting deterioration in muscle tone, muscle weakness and atrophy, even in cases in which the user has impaired ability to actively lift the foot to bring the foot into a desired angle with respect to the shin.

Additionally, or alternatively, due to the spring action of leaf spring assemblies 22 (and 220 described herein below), a load is relived from the foot of the user, making it easier for the user to continue to raise foot 10 from a position of reduced plantar flexion. Thus, contributing to rehabilitation of the user.

Further additionally, or alternatively, the spring action of leaf spring assemblies 22 (and 220 described herein below), assist in correcting impaired dorsiflexion by actively assist in in raising of foot 10.

Furthermore, as shown in FIG. 3B, middle portion 36 generally does not contact ankle joint 14 (also in the open state thereof), thus ankle joint 14 is not fixed or restricted by the leaf spring assembly. Accordingly, use of the leaf spring assembly allows increased rotation amplitude of ankle joint 14 in at least in the, sagittal, frontal and transverse planes.

Figure 4A:
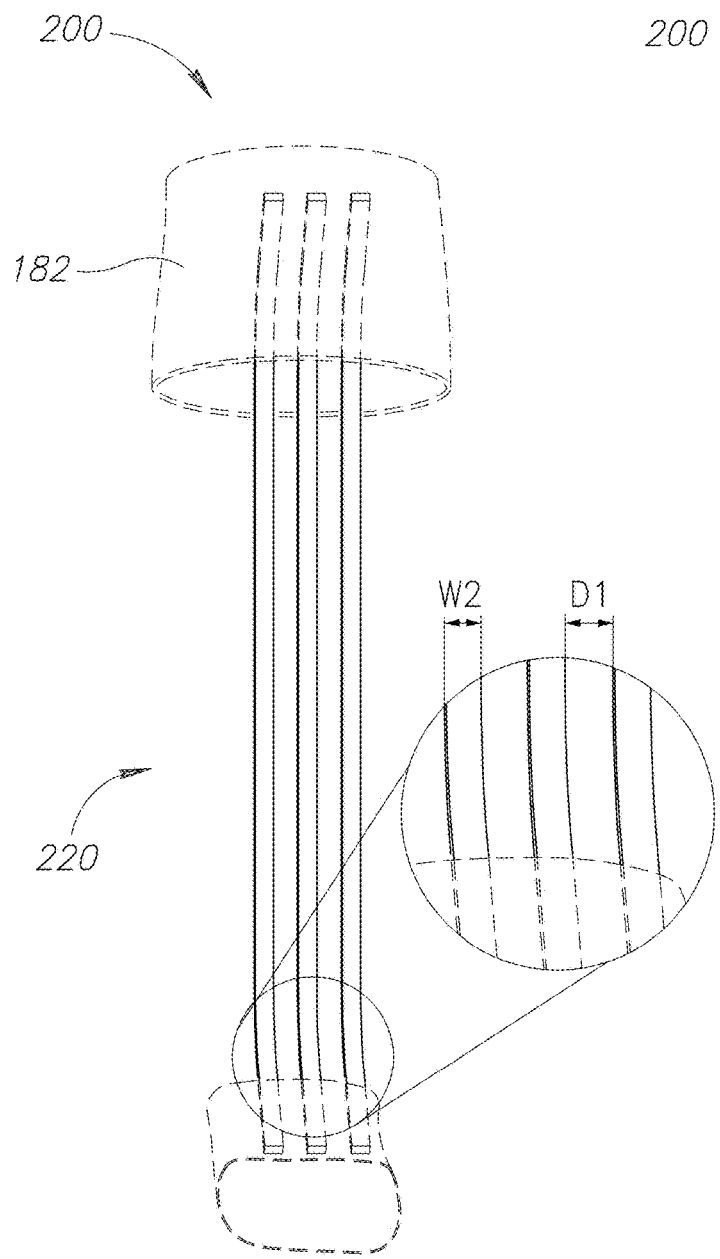
FIG. 4A is a schematic illustration of apparatus comprising a leaf spring assembly comprising multiple leaf springs in accordance with some embodiments of the present invention.

Reference is now made to FIG. 4A, which is a schematic illustration of apparatus 200 comprising a leaf spring assembly 220 in accordance with some embodiments of the present invention.

In some embodiments, leaf spring assembly 220 comprises more than one leaf spring assembly (e.g., a plurality of leaf springs assemblies 22). Typically, each one of springs assemblies 22 comprising a plurality of leaves.

As shown in FIG. 4A, for some embodiments, leaf spring assembly 220 comprises a first central leaf spring assembly 222, and a second leaf spring assembly 224 and a third leaf spring assembly 226, which are disposed alongside of central leaf spring assembly 222. Typically, each one of leaf springs 222, 224 and 226 comprise a plurality of elastic leaves 40. The number of leaves 40 in leaf springs assemblies 222, 224 and 226 may vary with respect to each other or be the same. For example, optionally, central leaf spring assembly 222 comprises a greater number of leaf springs 40 than each one of second and third leaf springs assembly 224 and 226. For example, first leaf spring assembly 222 comprises between 2-10 leaf springs 40 and second and third leaf springs assemblies 224 and 226 each comprise 2-5 leaf springs 40. Alternatively, leaf springs assembly 222 comprises a smaller number of leaf springs 40 than second and third leaf springs assemblies 224 and 226. Further alternatively, leaf springs assemblies 222, 224 and 226 comprise the same number of leaf springs 40.

By way of illustration and not limitation, leaf springs 222, 224 and 226 each have a width W2 of 1-40, mm e.g., 5-20 mm, e.g., 10-15 mm. It is noted that any suitable width can be used. For some embodiments, a distance D1 between central leaf spring 222 and second and third leaf springs 224 and 226 is 1-10 cm, e.g., 1-5 cm.

For some embodiments, each leaf 40 has a thickness T1 of 0.1-0.5 mm, e.g., 0.3 mm when unconstrained, and a weight of 5-10 grams, e.g., 8-9 grams, e.g., 8.7 grams. For some embodiments a minimum weight of leaf spring assembly 220 is 5-10 grams. For some embodiments, a total weight of leaf spring assembly 220 is between 5-40 grams, e.g., 25 grams.

In some embodiments, apparatus 200 further comprises a leaf spring-coupling element for coupling leaf spring assembly 220 to the user. For example, apparatus 200 comprises an upper spring-coupling element 182, e.g., a flexible cuff or a strap, configured to at least partially surround and conform to the shape of an upper portion of the limb, e.g., a portion of shin 16, in order to secure assembly 220 to the shin of the user. Additionally, apparatus 200 may comprise a lower leaf spring-coupling element 184, e.g., a flexible cuff or a strap, configured to at least partially surround and conform to the shape of a lower portion of the limb, e.g., ankle joint 14 or foot 10, in order to secure assembly 22 to a lower portion of leg 12. It is noted that apparatus 200 provides enhanced attachment to the foot 10 and shin 16 and facilitates optimal pressure distribution.

It is further noted that upper and lower leaf spring-coupling element 182 and 184 may also be used with leaf spring assembly 22, described hereinabove with reference to apparatus 20 in FIGS. 2A-B.

Figure 4B:
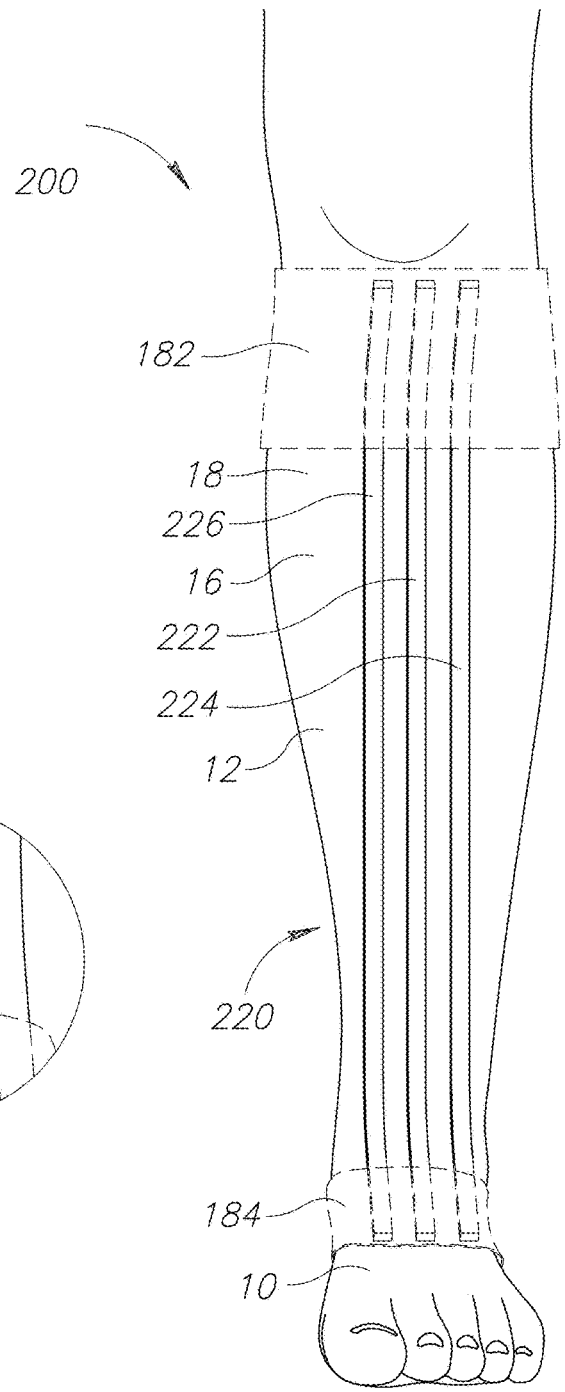
FIGS. 4B-C are schematic illustrations of the leaf spring assembly of FIG. 4A positioned on a lower leg of the subject, in accordance with some embodiments of the present invention.
Figure 4C:
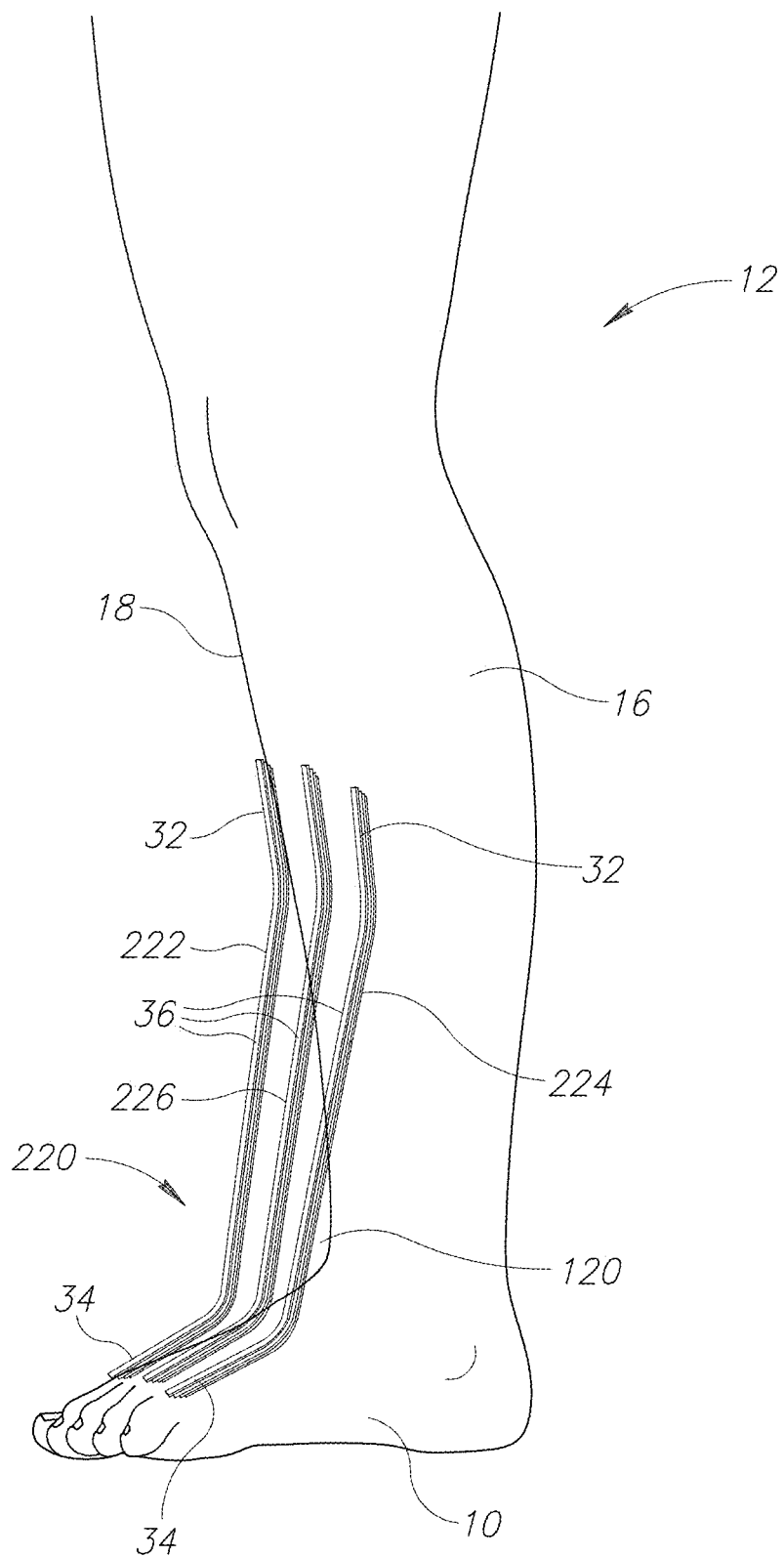

Reference is now made to FIGS. 4B-C which are schematic illustrations of a front view (FIG. 4B) and a side view (FIG. 4C) of leaf spring assembly 220 positioned on a lower leg 12 for maintaining foot 10 at a desired angle with respect to shin 16 of leg 12, in accordance with some embodiments of the present invention. Each leaf spring assembly 222, 224 and 226 is shaped to define a first end 32, and second end 34 and a middle portion 36 disposed between first end 32 and second end 34.

Leaf spring assembly 220 is placed against an outer surface 18 of the anterior side of leg 12 such that first end 32 is placed against a first location on shin 16, and second end 34 is placed against a second location on the dorsal side of foot 10. As shown, when leaf spring assembly 220 is constrained between shin 16 and the dorsal side of foot 10, middle portion 36 of each leaf spring assemblies 222, 224 and 226 generally does not contact leg 12, thereby forming gap 120 between the middle portion of leaf spring 220 leg 12 and ankle joint 14. Accordingly, leaf spring assembly 220, allows rotation at the ankle joint and typically facilitates increased ankle joint rotation amplitude in, for example, the transverse plane, and does not limit dorsiflexion in the sagittal plane, and does not limit eversion in the frontal plane.

Due to the spring action, leaf spring assembly 220 assists in correcting involuntary, excessive plantar flexion. For example, due to use of leaf spring assembly 220, plantar flexion is decreased to an angle of 10-15 degrees Thereby, leaf spring assembly 220 reduces foot drop by correcting the angle between foot 10 and shin 16 in a sagittal plane (angle theta).

Additionally, leaf spring assembly 220 assists in correcting impaired outward rotation of the foot (eversion) and inward rotation of the foot (inversion). For example, in order to assist a user suffering from impaired foot eversion leaf spring assembly 220 is configured to relieve a load from muscles of the user responsible for eversion, thereby facilitating eversion.

In some embodiments, central leaf spring 222 of leaf spring assembly 220 assists in the limiting of plantar flexion, and side leaf spring 224 and 226 correct impaired eversion, inversion and reduce over-rotation rotation of the foot.

In FIG. 4C, leaf spring coupling elements 182 and 184 are not shown for clarity.

Reference is still made to in FIGS. 4A-C. It is noted that leaf spring assembly 220 is shown as having three leaf springs by way of illustration and not limitation. It is noted that leaf spring assembly 220 may comprise two leaf springs or more than three leaf springs.

Figure 5B:
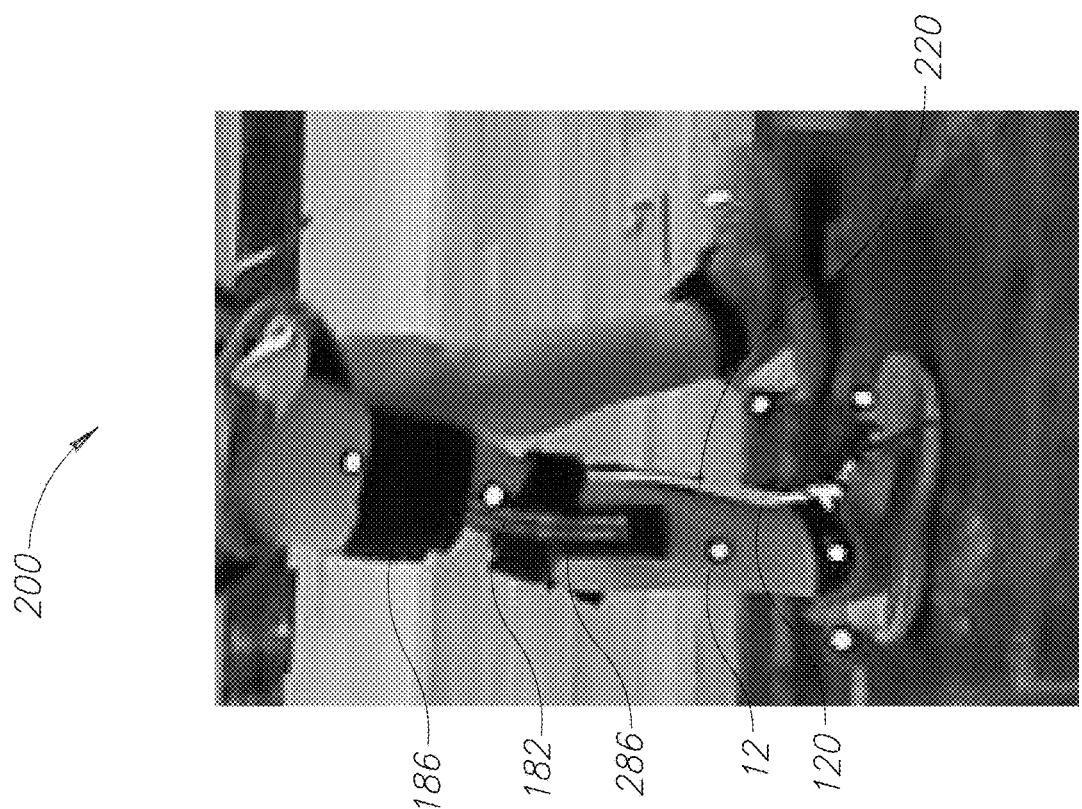
FIGS. 5A-B show apparatus comprising the leaf spring assembly being worn by a user during gait, in accordance with some embodiments of the present invention.
Figure 5A:
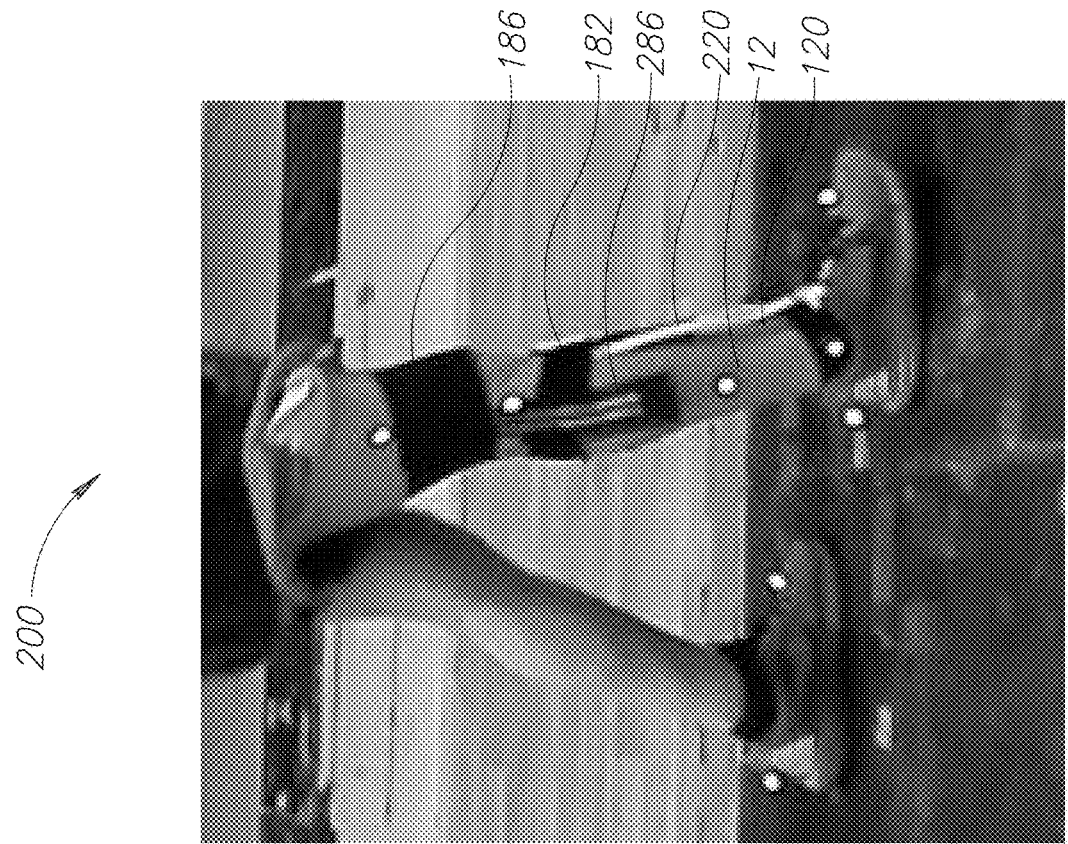

Reference is now made to FIGS. 5A-B which show apparatus 200 being used by a user during gait. As noted hereinabove, middle portion 36 of leaf spring assemblies 222, 224 and 226 generally do not contact the leg of the user, such that gap 120 is formed between the middle portion the leg. As shown in FIG. 5B, this is true also during gait when leaf spring assembly 220 is, flexed (deflected). In other words, also when middle portions 36 of leaf spring assemblies 222, 224 and 226 come nearer to leg 12 due to deflection of leaf spring assembly 220 during gait (during plantarflexion dorsiflexion, inversion or eversion), gap 120 is still maintained between middle portions 36 and leg 12, and ankle joint 14.

Figure 5C:
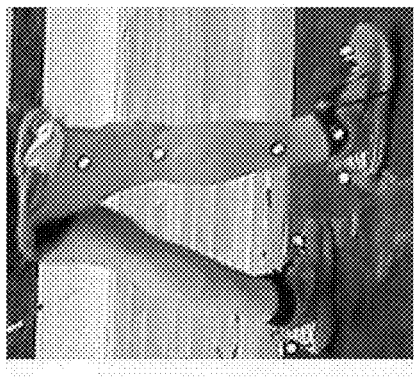
FIG. 5C shows gait of a subject suffering from foot drop, using the leaf spring assembly in accordance with some embodiments of the present invention, compared to not using a gait-supporting device.
Figure 5C:
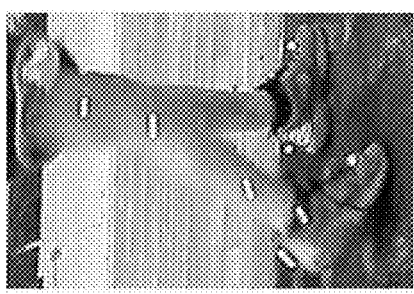
Figure 5C:
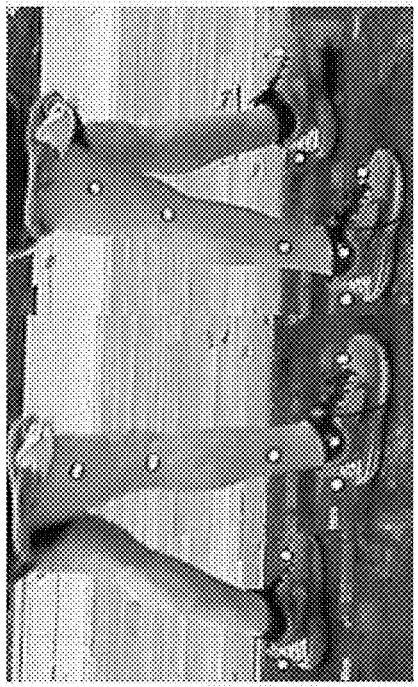
Figure 5C:
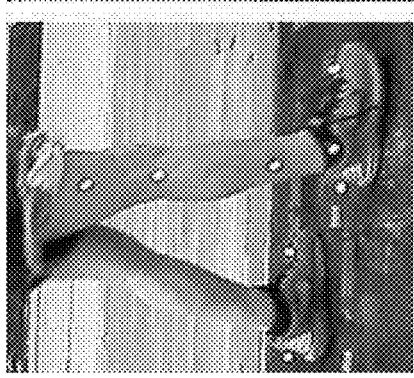
Figure 5C:
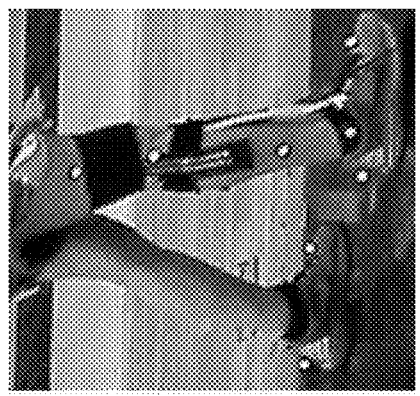
Figure 5C:
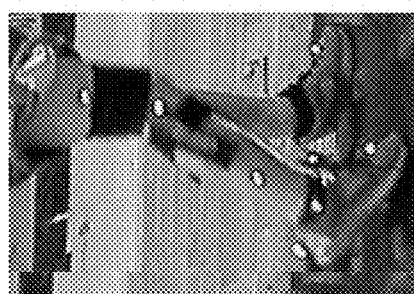
Figure 5C:
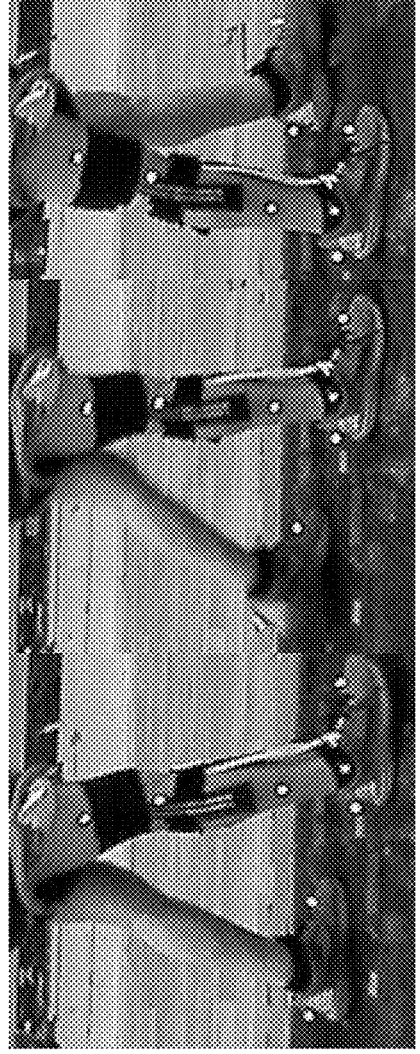

Reference is now made to FIG. 5C which shows gait of a subject suffering from foot drop, using apparatus 200 (lower panel) and not using a gait-supporting device (upper panel).

Generally, apparatus 200 (and apparatus 20 described hereinabove with reference to FIGS. 2A-B) are configured to improve gait of the user suffering from foot drop e.g., by reducing plantar flexion such that the foot slap, foot drag and foot collision with the ground during gait is inhibited.

Generally, during the stance phase of the gait cycle, apparatus 200 (and apparatus 20) assist the rolling or partial rolling from the heel to the toe by inhibiting foot slap and contribute to deceleration phase recovery. Additionally, or alternatively, apparatus 200 (and apparatus 20) correct an angle between the femur and the pelvis in sagittal plane in stance phase.

During the swing phase of the gait cycle apparatus 200 (and apparatus 20) typically inhibit forefoot collision with the ground and foot drag, thereby reducing the occurrence of loss of body balance and consequent falling.

More specifically, as shown in FIG. 5C, apparatus 200 enables the user to perform correct PushOff, and assists in detachment of the foot from the ground immediately following the PushOff phases. Additionally, the distance between the legs during in the FootFlat phase increases.

Further additionally, usage of apparatus 200 typically leads to the center of mass movement improvement between the HealStrike and FootFlat phases. When walking without apparatus 200, foot slap typically follows heel contact with the floor. Thus, as shown in FIG. 5C, usage of apparatus 200 leads to walking style correction.

Additionally, or alternatively, use of apparatus 200 (and apparatus 20) allows natural shock absorption during a normal gait cycle, and improves natural shock absorption during abnormal gait. Typically, subsequently to the foot hitting the ground during gait, a shock wave is initiated at the foot-footwear interface. This shock wave is propagated through the human musculoskeletal system and is attenuated and dissipated by the natural shock absorbers of the human musculoskeletal system, i.e. joints and soft tissues. Importantly, use of apparatus 200 (and apparatus 20) allow for this natural shock absorption to occur.

Reference is again made to FIGS. 5A-B. As shown, for some embodiments, apparatus 200 additionally comprises an elastic flexible knee cuff 186 shaped and sized to be worn at least in part around, below, or above a knee of the user, and at least one lateral flexible strap 286 connecting the upper spring-coupling element 182 to cuff 186. Typically, knee cuff 186 conforms to the natural shape of the knee. For some embodiments, an additional lateral flexible strap is used (not shown). For some embodiments, lateral strap 286 is disposed along an outer side of the shin and thigh and the additional flexible strap is disposed along an inner side of the shin and thigh.

Typically, knee cuff 186 stabilizes leaf spring assembly 220 through the flexible straps by adding additional support to apparatus 200 and inhibiting laxing of apparatus 200. Furthermore, in some embodiments knee cuff 186 is fixed to the leg, thereby fixing leaf spring assemblies 22 or 220 to the leg.

Additionally, or alternatively, knee cuff 186 supports the knee of the user and assists in bending (flexing and extending) of the knee, this contributing to rehabilitation of the user.

Additionally, or alternatively, knee cuff 186 typically stabilizes the leg and prevents excessive rotation of the foot during abduction and adduction.

It is further noted that flexible knee cuff 186 and the lateral straps may also be used with leaf spring 22 described hereinabove with reference to apparatus 20 in FIGS. 2A-B.

Reference is now made to FIGS. 2A-5C. It is noted that, importantly, leaf spring 22 and leaf spring assembly 220 are both corrective and rehabilitative. As described herein, leaf spring 22 and leaf spring assembly 220 improve gait of the user by limiting plantar flexion and maintaining a desired ankle angle. In some embodiments, leaf spring 22 and leaf spring assembly 220 limit plantar flexion to about 10-15 degrees, such that ankle angle theta is about 10-15 degrees. When using leaf spring assemblies 22 and 220, the user is encouraged to self-activate the user's muscle to continue lifting of the foot to bring the foot into any desired angle with respect to the shin (e.g., continue to raise the foot in dorsiflexion motion). Typically, this rehabilitative feature of leaf spring 22 and leaf spring assembly 220 contributes to improvement over-time in muscle strength and/or muscle memory and inhibits muscle weakness and complete dependency of the user on leaf spring 22 and leaf spring assembly 220. It is further noted, that by not continuously fixing the foot to be at a fixed angle with respect to the shin, muscle tone is maintained in the muscles of the lower leg thereby inhibiting deterioration in muscle tone, muscle weakness and atrophy, in cases in which the user has impaired ability to actively lift of the foot.

It is noted that use of leaf spring assembly 22 and leaf spring assembly 220, may improve muscle tone in healthy subject as well, e.g., athletes.

Additionally, as described herein, while limiting planter flexion, leaf spring assembly 22 and leaf spring assembly 220 typically do not restrict movement of the ankle in the transverse plane and typically does not restrict eversion in the frontal plane, as well as dorsiflexion in the sagittal plane, thereby reducing the probability of muscle atrophy and user dependency on leaf spring assembly 22 and leaf spring assembly 220.

Figure 6A:
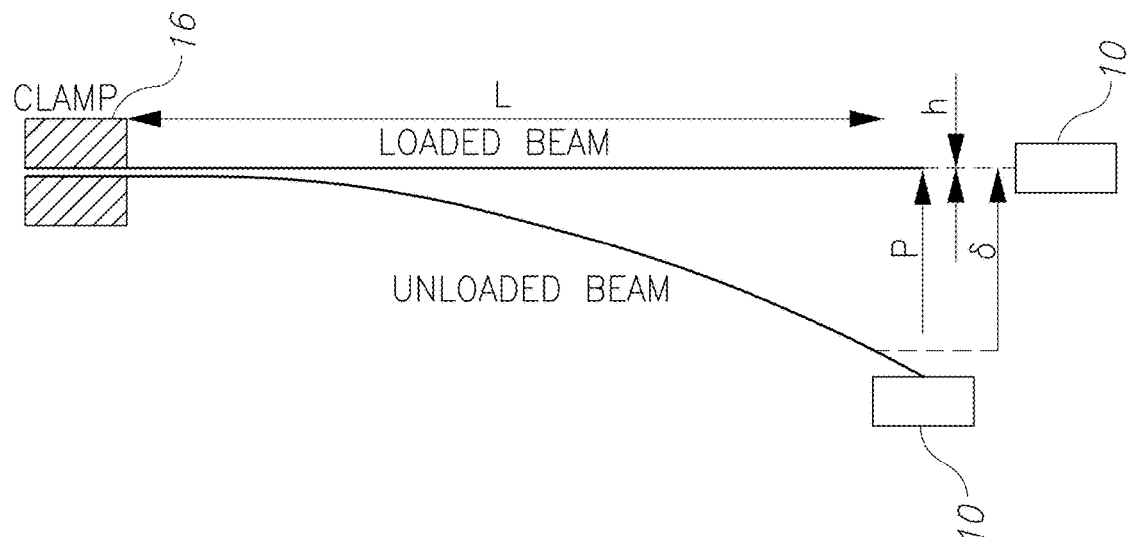
FIG. 6A is a schematic illustration of the leaf spring assembly, in accordance with some embodiments of the present invention.
Figure 6A:
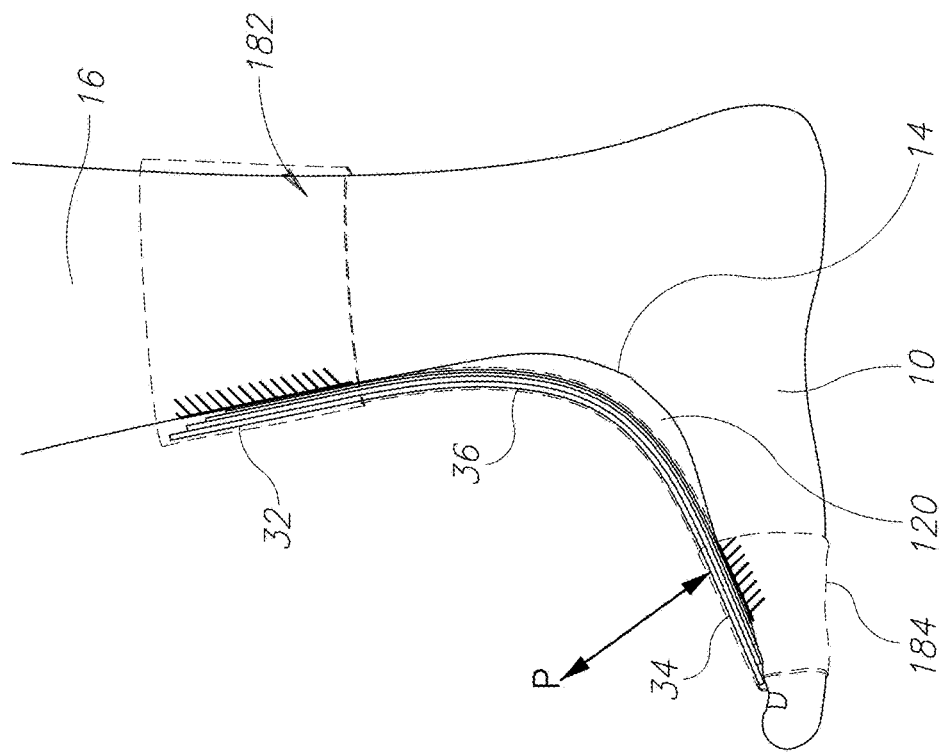

Reference is now made to FIG. 6A, which is schematic illustration of leaf spring assembly 22 or 220, being used by a user in accordance with some embodiments of the present invention. FIG. 6A additionally shows a diagram modeling the spring mechanism as fixed-free cantilever beam demonstrating the force applied on the spring by the foot of the user in an undeflected, straight, state (loaded beam, also shown in FIG. 2B), and in a deflected state (unloaded beam) assuming the natural shape of the spring (also as shown in FIG. 2C).

Typically, a stiffness of leaf spring assembly 22 and leaf spring assembly 220 are adjusted for each user. Advantageously, use of a leaf spring allows adjustment for each user by varying the stiffness of the leaf spring e.g., by adjusting a number of leaves 40. Typically, a suitable number of multiple individual leaves 40 are attached and fixed, or stacked to, one to another achieve the required stiffness per user.

By way of illustration and not limitation, leaf spring assembly 22 and leaf spring assembly 220 (which comprises leaf springs 222, 224 and 226) are adjusted per user as follows:

Adjustment of constant (k) of leaf spring 22 and leaf spring assembly 220. In this way the constant of leaf spring 22 and leaf spring assembly 220 is tuned for a specific disorder of a specific user. For example, the spring constant for central leaf spring 222 is a first spring constant and the spring constant of side leaf spring 224 and 226 is a second spring constant, and the first spring constant is different from the second spring constant (in some embodiments, each one of leaf spring 222, 224, and 226 have different spring constants). For example, for assisting in impaired eversion of foot 10, the spring constant is increased for side leaf spring 224 (with respect to side leaf spring 226 and/or central leaf spring 222) in order to reduce inversion of the foot. Additionally, or alternatively, for assisting in impaired dorsiflexion, the spring constant of central leaf spring 222 is increased in order to inhibit plantar flexion beyond 10-15 degrees.

In FIG. 6A first and second spring ends 32 and 34 have a fixed connection to foot 10 and shin 16 (the fixed point of connection indicated by CLAMP in the diagram), and shin 16 works as a wall, and foot 10 works as a mass applied to spring end 34 (such that, middle portion 36 works). Thus, as shown in the diagram in FIG. 6A, the spring mechanism can be modeled as fixed-free cantilever beam with rectangular cross section, as follows:

L—straight spring part length.
b—linear spring width.
h—linear spring thickness.
P—force applied to the end of straight spring part by the foot mass.
δ—straight spring part deflection
k—spring coefficient I—moment of inertia
E—Young's Modulus It is noted that when a double-headed arrow is shown to indicate the force P applied to the spring when the spring is positioned on the leg, P is indicative of the total force that is applied to the spring.

Typically, the spring constant (k) for an individual leaf 40 in leaf spring 22 and in leaf spring assembly 220 is calculated using the following formula:

$$\begin{cases} k = \dfrac{P}{\delta} \\ \delta_{max} = \dfrac{P \cdot L^3}{3 \cdot E \cdot I} \Leftrightarrow k = \dfrac{E \cdot b \cdot h^3}{4 \cdot L^3} \\ I = \dfrac{b \cdot h^3}{12} \end{cases}$$

For calculation of the constant of leaf spring 22 and leaf spring assembly 220 which comprise a plurality of leaves 40, a sum of the spring constants is calculated. Generally, leaves 40 are parallel to each in leaf spring assembly 22 and in each one of leaf springs 222, 224 and 226. Additionally, for the purposes of the below calculation, each leaf 40 has the same spring constant, geometry and raw material. Thus, according to classical mechanics, total springs constant in parallel connection is a sum of the individual springs contact, that is calculated using the following formula:

$$\begin{cases} k_{total} = \sum_{i=1}^{n} k_i \\ k_1 = k_2 = \ldots = k_n \end{cases} \Leftrightarrow k_{total} = n \cdot k$$

Figure 6B:
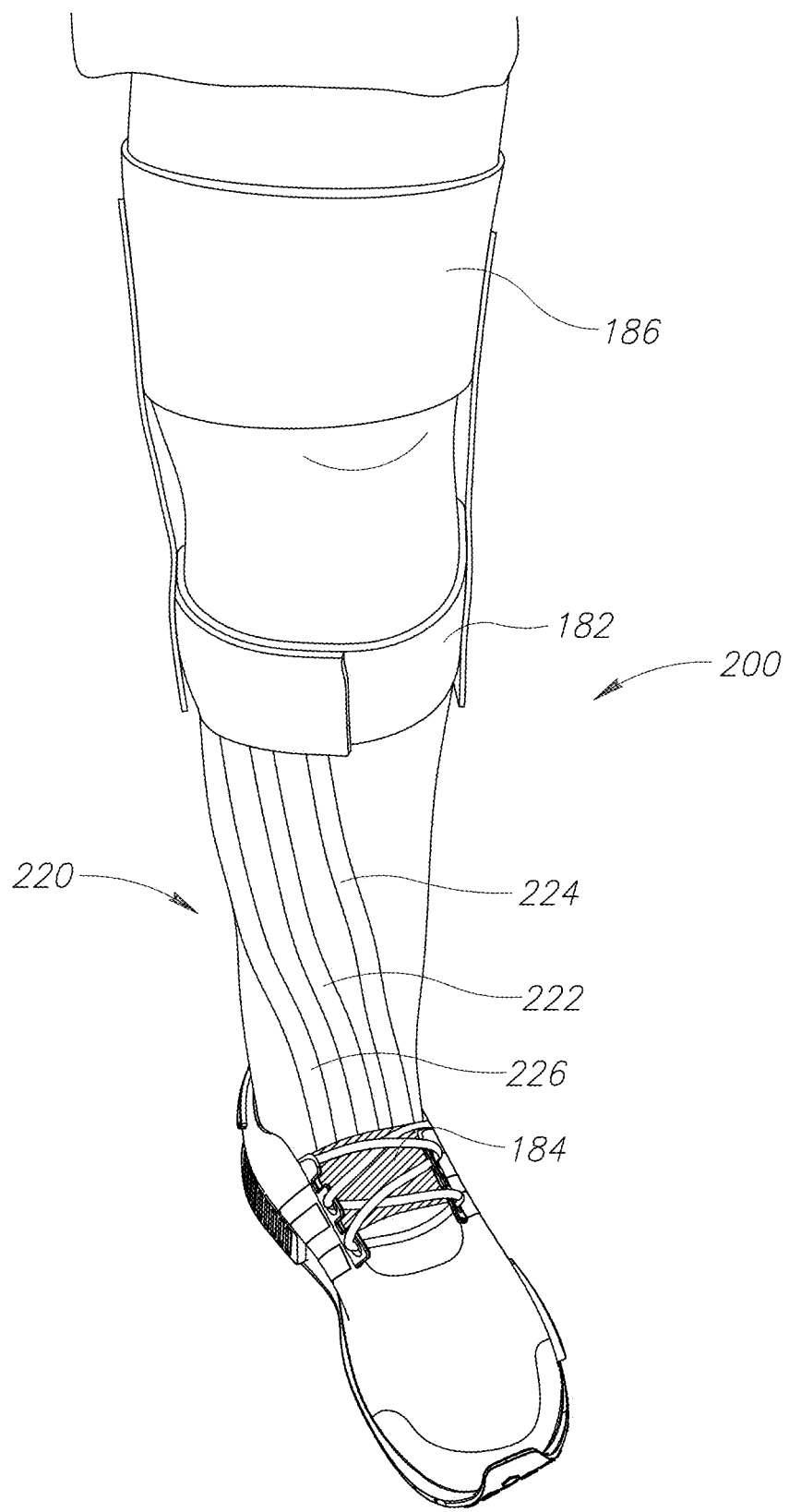
FIG. 6B shows pre-loading of the leaf spring assembly, in accordance with some embodiments of the present invention.

Reference is now made to FIG. 6B, which shows preloading of the leaf spring assembly 220, in accordance with some embodiments of the present invention. Typically, preload tuning is done for each user individually. For example, for assisting in impaired eversion, the preloading of assemblies 22 and 220 is adjusted to reduce foot inversion (FIG. 6B).

Figure 6C:
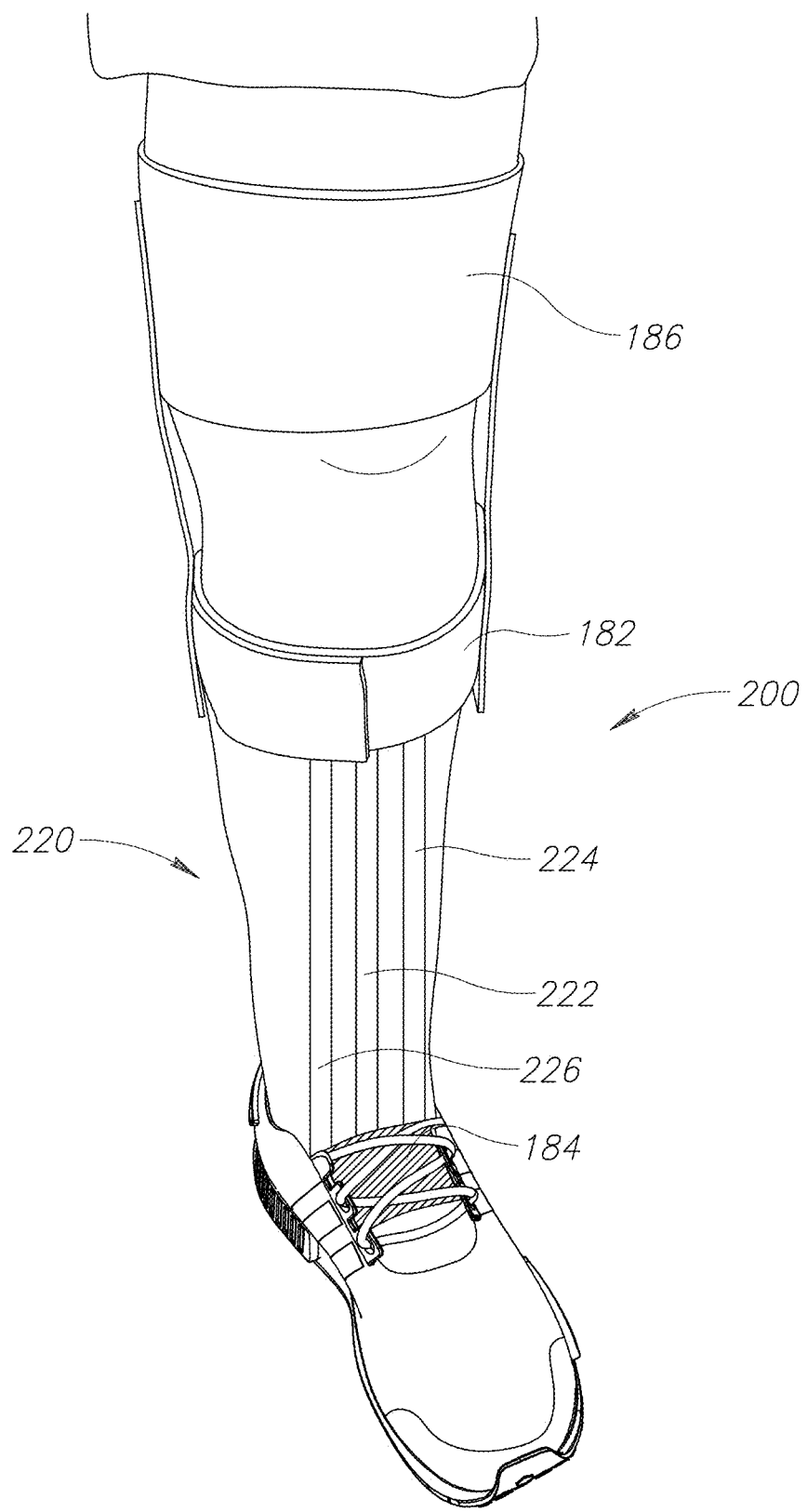
FIG. 6C is a schematic illustration of the leaf the leaf spring assembly, in accordance with some embodiments of the present invention.

FIG. 6C shows apparatus 200 comprising leaf spring assembly 220, worn by a user with a shoe of the user (without pre-loading).

Figure 7A:
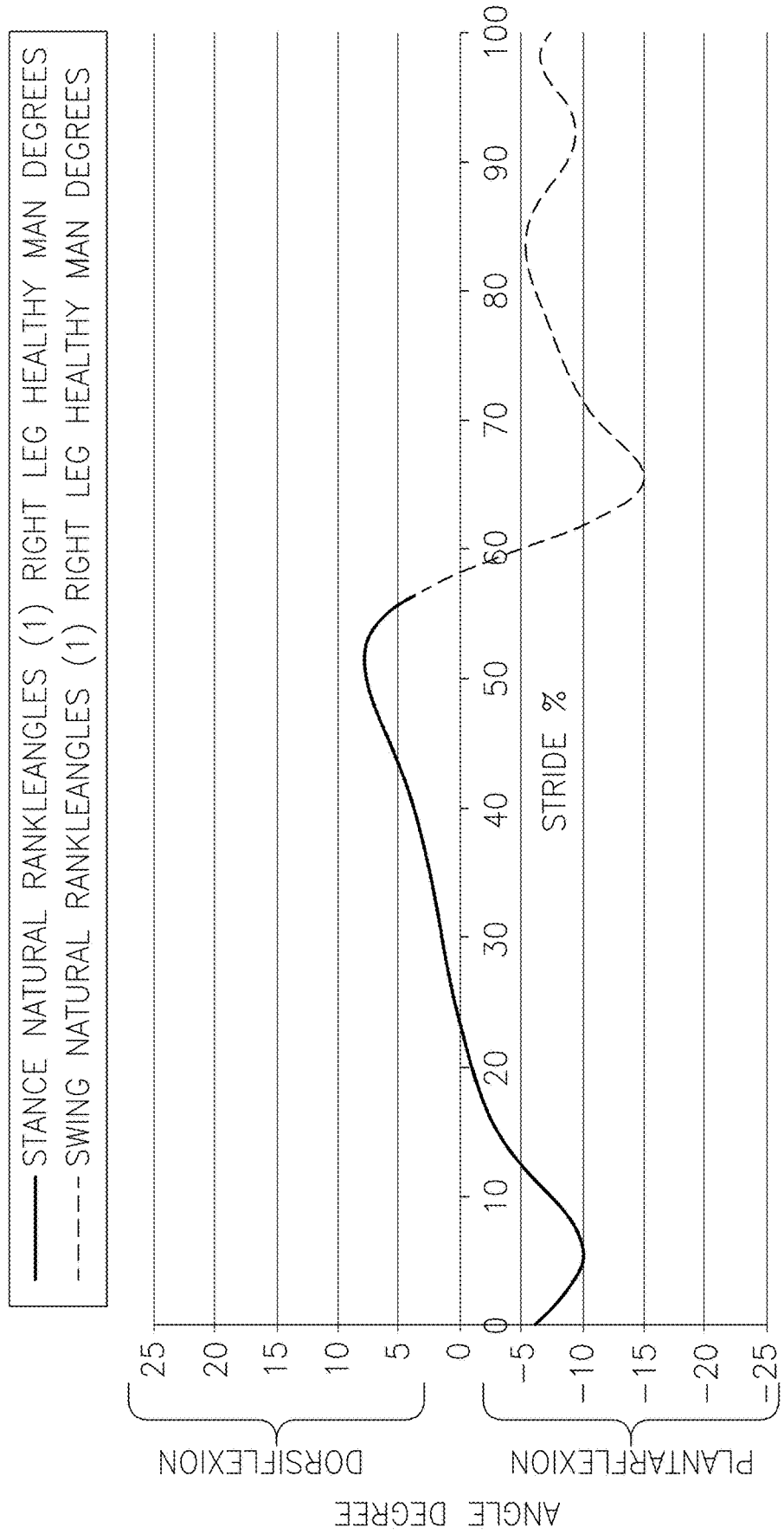
FIGS. 7A-C are graphs representing a trajectory of the ankle angle during the stance phase and swing phase of gait in a healthy subject (FIG. 7A), and in a subject suffering from foot drop using the leaf spring assembly in accordance with some embodiments of the present invention compared to use of a known gait supporting device, and to natural walking without a support device (FIGS. 7B-C).
Figure 7B:
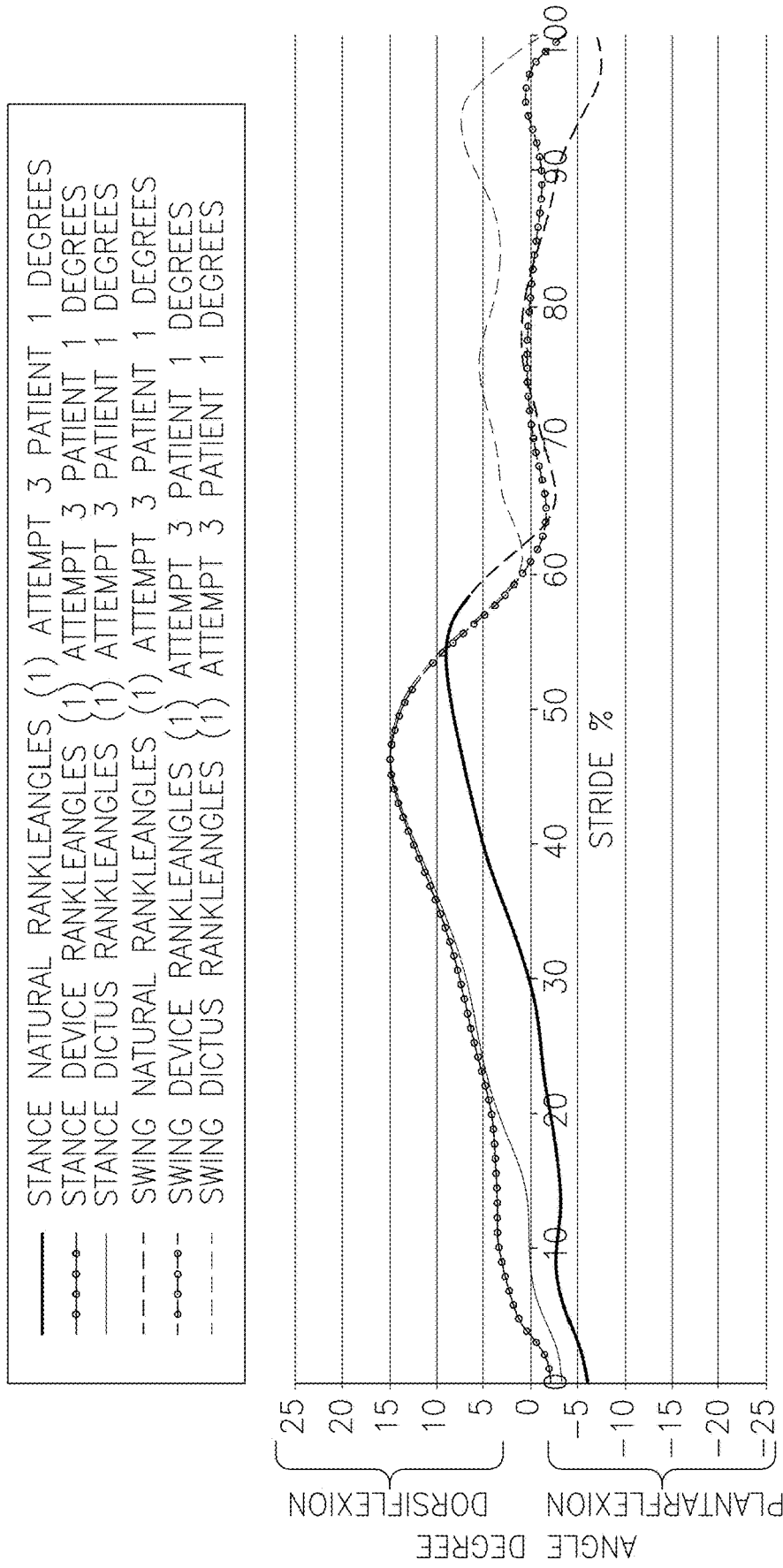
Figure 7C:
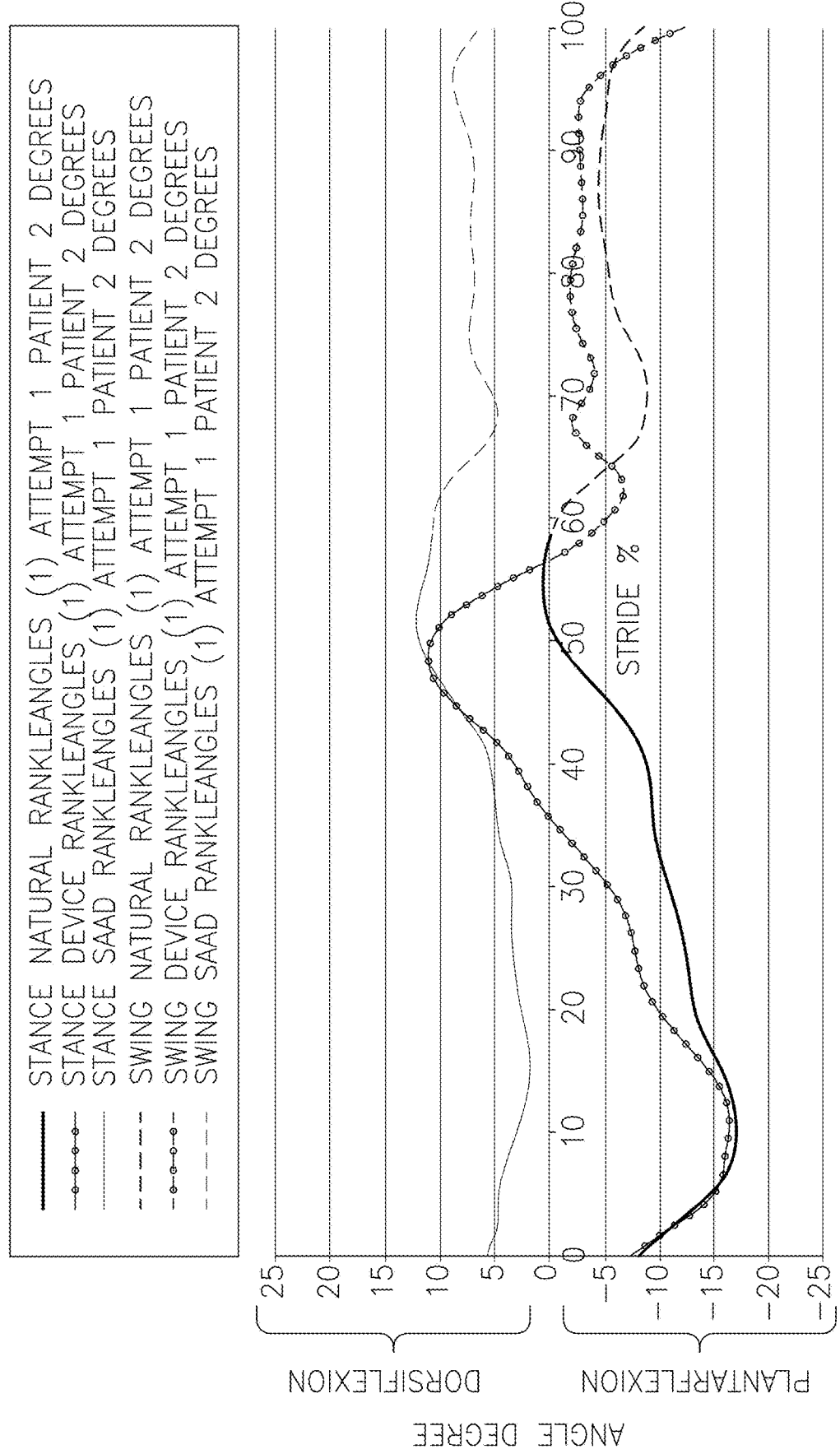

Reference is now made to FIGS. 7A-C which are graphs representing a trajectory of the ankle angle (i.e., the angle between the foot and the shin in the sagittal plane, i.e., angle theta shown in FIGS. 3A-B) during the stance phase and swing phase of gait in a healthy subject (FIG. 7A), and in a subject suffering from foot drop using leaf spring assembly 220 in accordance with some embodiments of the present invention compared to use of a known gait supporting device, and to natural walking without a support device (FIGS. 7B-C).

FIG. 7A is representative of the right ankle angle trajectory of the healthy subject during the stance phase and swing phase of gait. As shown, at initial contact, the ankle joint is neutral or slightly plantarflexed 3° to 5°. From initial contact to loading response, the ankle plantarflexes (i.e., extends) to a maximum of 7° as the foot is lowered to the supporting surface. Throughout midstance, the ankle dorsiflexes (i.e., flexes) to a maximum of 15° as the lower leg rotates anteriorly and medially over the supporting foot. During terminal stance and pre-swing, the ankle plantarflexes to approximately 15° as body weight is transferred onto the contralateral limb. Immediately following toe off, the ankle rapidly dorsiflexes to the neutral position to attain toe clearance and then may plantarflex slightly during terminal swing in preparation for initial contact.

FIG. 7B, is representative of the ankle angle trajectories during the stance phase and swing phase of gait of a subject suffering from foot drop, (i) using leaf spring assembly 220 in accordance with some embodiments of the present invention (ii) using of a known gait supporting device (Dictus Band Ankle Strap), and (iii) natural walking without a support device. As shown, during swing phase, using the leaf spring assembly in accordance with some embodiments of the present invention, resembles gait of the healthy subject as shown in FIG. 7A. Additionally, using leaf spring assembly 220 in accordance with some embodiments of the present invention, at least partially resembles a normal ankle joint rotation trajectory in the sagittal plane.

FIG. 7C is representative of the ankle angle trajectories during the stance phase and swing phase of gait of a subject suffering from foot drop, (i) using leaf spring assembly 220 in accordance with some embodiments of the present invention (ii) using of a known gait supporting device (SAAD), and (iii) natural walking without a support device. As shown, when using leaf spring assembly 220, amplitude and resembled that of the healthy subject (FIG. 7A). Additionally, use of leaf spring assembly 220 results in close to normal ankle joint rotation trajectory in the sagittal plane. In contrast, it appears, based on the graph in FIG. 7C, that the SAAD device significantly limits the ankle movement in the sagittal plane.

In summary, experimental results show that use of leaf spring assembly 220 in accordance with some embodiments of the present invention, result in ankle angle rotation between the foot and the shin at least in the sagittal plane resembling that of a healthy subject. Additionally, angle rotation between the femur and the pelvis in the sagittal plane during the stance phase is comparable to that of a healthy subject. Thus, use of leaf spring assembly 220 in accordance with some embodiments of the present invention, improves the gait of users suffering from foot drop and improve normal ankle joint rotation trajectory at least in the sagittal, transverse and frontal planes.

Reference is again made to FIGS. 2A-6B. It is noted that use of apparatus 20 and apparatus 200 is not limited to users suffering from impaired gait or foot drop or any other gait disorder. For example, apparatus 20 and 200 are also configured for use by subjects that suffer from an ankle injury or subject with diabetes. Additionally, or alternatively, apparatus 20 and 200 are also configured for use in a healthy user to assist in gait and relieve a load from the user, e.g., athletes.

Reference is again made to FIGS. 2A-6B. It is noted that the leaf spring assemblies described herein, are described by way of illustration and not limitation. The scope of embodiments of the present invention includes the use of any other type of spring, e.g., a helical spring, any type of linear spring, variable rate springs, etc. Additionally, or alternatively, the scope of embodiments of the present invention include the use of different types and sizes of springs within a given spring assembly as described herein, as well as different spring geometries and raw materials within a given spring assembly.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. An apparatus comprising:
   two or more leaf spring assemblies,
   an elastic flexible knee cuff;
   an upper spring-coupling element connected to the two or more leaf spring assemblies; and
      at least one lateral flexible strap connecting the upper spring-coupling element to the elastic flexible knee cuff,
   wherein each leaf spring assembly comprises:
      (a) shaped to define a first end, a second end, and a middle portion comprising a plurality of layered leaf springs disposed between the first and second ends; and
      (b) configured to be placed across a joint of a user such that the first end is configured to be placed against a first location on a first side of the joint, and the second end is configured to be placed against a second location on a second side of the joint, and when each leaf spring from the plurality of layered leaf springs is constrained between the first and second locations:
         (i) the middle portion of each leaf spring is configured to bridge] a gap formed between the middle portion and the joint, and
         (ii) each leaf spring is configured to be constrained at a position of a first portion of a limb on the first side of the joint, such that, a desired angle is maintained with respect to a second portion of the limb on the second side of the joint,
   wherein a lateral distance is maintained between at least one middle leaf spring assembly and a neighbouring leaf spring assembly from the two or more leaf spring assemblies.

2. The apparatus according to claim 1, wherein the plurality of layered leaf springs comprises a first leaf spring and a second leaf spring, the second leaf spring being positioned alongside the first leaf spring.

3. The apparatus according to claim 2, wherein a first leaf spring assembly from the two or more leaf spring assemblies has a first spring constant, and a second leaf spring assembly from the two or more leaf spring assemblies has a second spring constant.

4. The apparatus according to claim 2, further comprising a third leaf spring assembly configured to be positioned alongside the at least two leaf spring assemblies.

5. The apparatus according to claim 1,
   wherein the joint includes an ankle joint, the first location includes a location on a shin of a subject and the second location includes a location on a dorsal side of a foot of the subject, and wherein
   the two or more leaf spring assemblies are configured to be placed against a leg such that the upper portion contacts the shin and the lower portion are configured to contact the dorsal side of the foot, and position of a foot of the subject is maintained at a desired angle with respect to the leg.

6. The apparatus according to claim 1, wherein each leaf spring of the plurality of layered leaf springs comprises a linear portion.

7. The apparatus according to claim 1, wherein the upper spring-coupling element is configured to couple each leaf spring, from the plurality of layered leaf springs, to the subject.

8. A method of using the apparatus as claimed in claim 1 comprising,
   positioning the two or more leaf spring assemblies including the plurality of layered leaves, against the first and second locations on an outer surface of an anterior side of a leg of a subject; and
   maintaining a position of a foot of the subject at the desired angle with respect to a shin of the subject by constraining the two or more leaf spring assemblies between the first and second locations.

9. An apparatus comprising;
   two or more leaf spring assemblies;
   an elastic flexible knee cuff;
   an upper spring-coupling element connected to the two or more leaf spring assemblies; and
   at least one lateral flexible strap connecting the upper spring-coupling element to the elastic flexible knee cuff,
   wherein each leaf spring assembly comprises:
      (a) shaped to define a first end, a second end, and a middle portion comprising a plurality of layered leaf springs disposed between the first and second ends; and
      (b) configured to be placed against an outer surface of an anterior side of a leg of a subject such that the first end is configured to contact a first location and the second end is configured to contact a second location, and when each leaf spring from the plurality of layered leaf springs is constrained between the first and second locations:
         (i) the middle portion of each leaf spring is configured to bridge a gap formed across an ankle joint between the middle portion and the leg, and (ii) each leaf spring is configured to be constrained at a position of a foot of the subject, such that, a desired angle is maintained with respect to the leg, wherein a lateral distance is maintained between at least one middle leaf spring assembly and a neighbouring leaf spring assembly from the two or more leaf spring assemblies.

10. The apparatus according to claim 9, further comprising a lower spring-coupling element configured to couple each leaf spring, from the plurality of layered leaf springs, to the subject.

11. The apparatus according to claim 10, wherein the upper spring-coupling element comprises an upper cuff coupled to the upper portion of a corresponding leaf spring assembly and configured to surround at least a portion of a lower leg of the subject.

12. The apparatus according to claim 10, wherein the lower spring-coupling element comprises a lower cuff coupled to the lower portion of a corresponding leaf spring assembly and configured to surround an ankle of the subject.

13. The apparatus according to claim 9, wherein the plurality of layered leaf springs comprises a first leaf spring and a second leaf spring positioned alongside the first leaf spring.

14. The apparatus according to claim 13, wherein the first leaf spring assembly from the two or more leaf spring assemblies has a first spring constant, and the second leaf spring assembly from the two or more leaf spring assemblies has a second spring constant.

15. The apparatus according to claim 13, further comprising a third leaf spring assembly configured to be positioned alongside the two or more leaf spring assemblies.

16. The apparatus according to claim 9, wherein the first location includes a shin of the subject and the second location includes a dorsal side of the foot of the subject, and wherein the two or more leaf spring assemblies is configured to be placed against the leg such that the upper portion is configured to contact the shin and the lower portion is configured to contact the dorsal side of the foot.

17. The apparatus according to claim 9, wherein the middle portion has a length of 10-20 cm, when the two or more leaf spring assemblies are unconstrained.

* * * * *